(12) United States Patent
Mateo De Acosta Del Rio et al.

(10) Patent No.: US 8,758,753 B2
(45) Date of Patent: Jun. 24, 2014

(54) GANGLIOSIDE ASSOCIATED RECOMBINANT ANTIBODIES AND THE USE THEREOF IN THE TREATMENT OF TUMORS

(75) Inventors: Cristina Maria Mateo De Acosta Del Rio, Ciudad de la Habana (CU); Josefa Lombardero Valladares, Ciudad de la Habana (CU); Lourdes Tatiana Roque Navarro, Ciudad de la Habana (CU); Alejandro Lopez Requena, Ciudad de la Habana (CU)

(73) Assignee: Centro de Inmunologia Molecular (CIM) (CU)

( * ) Notice: Subject to any disclaimer, the term of this patent is extended or adjusted under 35 U.S.C. 154(b) by 626 days.

(21) Appl. No.: 12/407,046

(22) Filed: Mar. 19, 2009

(65) Prior Publication Data

US 2010/0297008 A1 Nov. 25, 2010

Related U.S. Application Data

(62) Division of application No. 10/473,977, filed as application No. PCT/CU02/00003 on Apr. 8, 2002, now abandoned.

(30) Foreign Application Priority Data

Apr. 6, 2001 (CU) .......................................... 84/01

(51) Int. Cl.
| | | |
|---|---|---|
| *A61K 39/395* | (2006.01) | |
| *C07K 16/42* | (2006.01) | |
| *C12N 5/10* | (2006.01) | |
| *G01N 33/577* | (2006.01) | |
| *C12N 5/09* | (2010.01) | |
| *G01N 33/68* | (2006.01) | |
| *C12N 15/13* | (2006.01) | |
| *C12N 5/0781* | (2010.01) | |
| *G01N 33/574* | (2006.01) | |
| *C12N 5/16* | (2006.01) | |

(52) U.S. Cl.
CPC ....... *A61K 39/39566* (2013.01); *C07K 16/4208* (2013.01); *C07K 16/4266* (2013.01); *C12N 5/0694* (2013.01); *G01N 33/577* (2013.01); *G01N 33/686* (2013.01); *C07K 2317/24* (2013.01); *C07K 2317/76* (2013.01); *C12N 5/163* (2013.01); *G01N 33/57415* (2013.01); *G01N 2033/57403* (2013.01); *G01N 2800/7028* (2013.01)
USPC .................. 424/131.1; 424/130.1; 424/133.1; 424/137.1; 424/138.1; 424/141.1; 424/155.1; 424/174.1; 435/69.1; 435/70.21; 435/328; 435/329; 435/330; 435/344; 530/387.3; 530/387.5; 530/387.7; 530/388.1; 530/388.8

(58) Field of Classification Search
CPC ........... A61K 39/395; A61K 39/39566; C07K 16/42; C07K 16/4208; C07K 16/4266; C07K 2317/24; C07K 2317/76; C12N 5/06; C12N 5/0694; C12N 5/163; G01N 33/574; G01N 33/57415; G01N 33/577; G01N 33/686; G01N 2033/57403; G01N 2800/7208
USPC ............. 435/69.1, 70.21, 328, 329, 330, 344; 530/387.3, 387.5, 387.7, 388.1, 388.8; 424/9.1, 9.34, 130.1, 137.1, 138.1, 424/141.1, 155.1, 174.1, 131.1, 133.1
See application file for complete search history.

(56) References Cited

U.S. PATENT DOCUMENTS

| | | | | |
|---|---|---|---|---|
| 5,712,120 A | * | 1/1998 | Rodriguez et al. ........... | 435/69.6 |
| 5,817,513 A | * | 10/1998 | Lopez et al. ................. | 435/329 |
| 6,063,379 A | * | 5/2000 | Vazguez Lopez et al. . | 424/130.1 |

OTHER PUBLICATIONS

Owens et al., 1994. The genetic engineering of monoclonal antibodies. J. Immunolog. Meth. 168: 149-165.*

* cited by examiner

*Primary Examiner* — Mark Shibuya
*Assistant Examiner* — James L Grun
(74) *Attorney, Agent, or Firm* — Lackenbach Siegel, LLP

(57) ABSTRACT

The present invention is related to the obtaining of modified antibodies by means of DNA recombinant technology from the murine monoclonal antibody P3 (MAb P3), produced by the hybridoma cell line deposited under Budapest Treaty with accession number ECACC 94113026, and from its anti-idiotype murine monoclonal antibody 1E10(MAbai 1E10), produced by the hybridoma cell line with deposit number ECACC 97112901, with the objective of achieving monoclonal antibodies which preserve the biological function of specifically binding the antigen of the original antibodies, but being at the same time less immunogenic. The chimeric antibodies of the invention contain the variable domains of the murine immunoglobulin and the constant regions of the human immunoglobulin; and those humanized, besides containing the constant regions of the human immunoglobulins, are modified in the murine framework regions (FRs), in particular, in those zones that could be in a T cell antigenic site, so that several positions of the FRS are human as well. These antibodies can be used in the diagnosis and therapy of different types of tumors. The present invention is also related to the use of the antibodies for therapeutic and diagnostic purposes.

3 Claims, 5 Drawing Sheets

Figure 1

|  | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 |
|---|---|---|---|---|---|---|---|---|---|---|---|---|---|---|---|---|---|---|---|---|---|---|---|---|---|
|  | Q | V | Q | L | K | E | S | G | P | G | L | V | A | P | S | Q | S | L | S | I | T | C | T | V | S |
| VH P3 | CAG | GTG | CAG | CTG | AAG | GAG | TCA | GGA | CCT | GGC | CTG | GTG | GCA | CCC | TCA | CAG | AGC | CTG | TCC | ATC | ACA | TGC | ACT | GTC | TCT |

CDR1

|  | 26 | 27 | 28 | 29 | 30 | 31 | 32 | 33 | 34 | 35 | 35a | 35b | 36 | 37 | 38 | 39 | 40 | 41 | 42 | 43 | 44 | 45 | 46 | 47 | 48 |
|---|---|---|---|---|---|---|---|---|---|---|---|---|---|---|---|---|---|---|---|---|---|---|---|---|---|
|  | G | F | S | L | S | R | Y | G | V | H |  |  | W | V | R | Q | P | P | G | K | G | L | E | W | L |
| VH P3 | GGG | TTC | TCA | TTA | TCC | AGA | TAT | AGT | GTA | CAC |  |  | TGG | GTT | CGC | CAG | CCT | CCA | GGA | AAG | GGT | CTG | GAG | TGG | CTG |

CDR2

|  | 49 | 50 | 51 | 52 | 52a | 52b | 52c | 53 | 54 | 55 | 56 | 57 | 58 | 59 | 60 | 61 | 62 | 63 | 64 | 65 | 66 | 67 | 68 | 69 | 70 |
|---|---|---|---|---|---|---|---|---|---|---|---|---|---|---|---|---|---|---|---|---|---|---|---|---|---|
|  | G | M | I | W |  |  |  | G | G | G | S | T | D | Y | N | S | A | L | K | S | R | L | S | I | S |
| VH P3 | GGA | ATG | ATA | TGG |  |  |  | GGT | GGT | GGA | AGC | ACA | GAC | TAT | AAT | TCA | GCT | CTC | AAA | TCC | AGA | CTG | AGC | ATC | AGC |

|  | 71 | 72 | 73 | 74 | 75 | 76 | 77 | 78 | 79 | 80 | 81 | 82 | 82a | 82b | 82c | 83 | 84 | 85 | 86 | 87 | 88 | 89 | 90 | 91 | 92 |
|---|---|---|---|---|---|---|---|---|---|---|---|---|---|---|---|---|---|---|---|---|---|---|---|---|---|
|  | K | D | N | S | K | S | Q | V | F | L | K | M | N | S | L | Q | T | D | D | T | A | M | Y | Y | C |
| VH P3 | AAG | GAC | AAC | TCC | AAG | AGC | CAA | GTT | TTC | TTA | AAA | ATG | AAC | AGT | CTG | CAA | ACT | GAT | GAC | ACA | GCC | ATG | TAC | TAC | TGT |

CDR3

|  | 93 | 94 | 95 | 96 | 97 | 98 | 99 | 100 | 100a | b | c | d | e | f | 101 | 102 | 103 | 104 | 105 | 106 | 107 | 108 | 109 |
|---|---|---|---|---|---|---|---|---|---|---|---|---|---|---|---|---|---|---|---|---|---|---|---|
|  | A | R | S | G | V | R | E | G | R | A | Q | A | W | F | A | Y | W | G | Q | G | T | L | V |
| VH P3 | GCC | AGA | AGT | GGG | GTA | CGA | GAG | GGA | AGG | GCC | CAG | GCC | TGG | TTT | GCT | TAC | TGG | GGC | CAA | GGG | ACT |  |  |
|  | CTG | GTC |  |  |  |  |  |  |  |  |  |  |  |  |  |  |  |  |  |  |  |  |  |

Figure 2

|  | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 |
|---|---|---|---|---|---|---|---|---|---|---|---|---|---|---|---|---|---|---|---|---|---|---|---|---|---|
|  | D | I | V | M | T | Q | S | H | K | F | M | S | T | S | V | G | D | R | V | S | I | T | C | K | A |
| VkP3 | GAC | ATT | GTG | ATG | ACC | CAG | TCT | CAC | AAA | TTC | ATG | TCC | ACA | TCA | GTA | GGA | GAC | AGG | GTC | AGC | ATC | ACC | TGC | AAG | GCC |

CDR1

|  | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 |
|---|---|---|---|---|---|---|---|---|---|---|---|---|---|---|---|---|---|---|---|---|---|---|---|---|---|
|  | S | Q | D | V | S | T | A | V | A | W | Y | Q | Q | K | P | G | Q | S | P | K | L | L | I | Y | S |
| VkP3 | AGT | CAG | GAT | GTG | AGT | ACT | GCT | GTA | GCC | TGG | TAT | CAA | CAG | AAA | CCA | GGA | CAA | TCT | CCT | AAA | CTA | CTG | ATT | TAC | TCG |

CDR2

|  | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 |
|---|---|---|---|---|---|---|---|---|---|---|---|---|---|---|---|---|---|---|---|---|---|---|---|---|---|
|  | A | S | Y | R | Y | T | G | V | P | D | R | F | T | G | S | G | S | G | T | D | F | T | F | T | I |
| VkP3 | GCA | TCC | TAC | CGG | TAC | ACT | GGA | GTC | CCT | GAT | CGC | TTC | ACT | GGC | AGT | GGA | TCT | GGG | ACG | GAT | TTC | ACT | TTC | ACC | ATC |

CDR3

|  | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 |
|---|---|---|---|---|---|---|---|---|---|---|---|---|---|---|---|---|---|---|---|---|---|---|---|---|---|
|  | S | S | V | Q | A | E | D | L | A | V | Y | Y | C | Q | Q | H | Y | S | T | P | W | T | F | G | G |
| VkP3 | AGC | AGT | GTG | CAG | GCT | GAA | GAC | CTG | GCA | GTT | TAT | TAC | TGT | CAG | CAA | CAT | TAT | AGT | ACT | CCG | TGG | ACG | TTC | GGT | GGA |

|  | 101 | 102 | 103 | 104 |
|---|---|---|---|---|
|  | G | T | K | L |
| VkP3 | GGC | ACC | AAG | CTG |

Figure 3

```
           10         20         30         40         50
VHP3   QVQLKESGPGLVAPSQSLSITCTVSGFSLSRYSVHWVRQPPGKGLEWLGMI-WGGGSTDY
       X:.:  :::  :.:  :..::  ..:..:::..:  :..:::::::::::::...:  .  :  .  v^
huhoVH QVELVESGGGVVZPGRSLRLSCAASGFTFSNYAMHWVRQPPGKGLEWVAVISYBGBBKYY
           10         20         30         40         50         60

60         70         80         90         100        110
VHP3   NSALKSRLSISKDNSKSQVFLKMNSLQTDDTAMYYCARSGVREGRAQAWFAYWG-GTLV
       ...:.:..::..:.::.  ..:.:::!:....::.:::::.     :   .:  :  :::  ::::
huhoVH ABSVKGRFTISRDBSKBTLYLQMNSLRAEBTAVYYCARDRPLYGBYRA-FNYWGQGTLV
           70         80         90         100        110
```

Figure 4

```
           10         20         30         40         50         60
VKP3   DIVMTQSHKFMSTSVGDRVSITCKASQDVSTAVAWYQQKPGQSPQLLIYSASYRYTGVPD
       ::  ::::  .  .:.::::::::.:::.::::.  :    :..X:.:::.....::::::   :::  .
huhoVK DIQMTQSPSSLSASVGDRVTITCRASQDI-TNYNWFQQRPGQAPKVLIYGASILETGVTS
           10         20         30         40         50

70         80         90         100
VKP3   RFTGSGSGTDFTFTISSVQAEDLAVYYCQQHYSTPWTFGGGTKL
       ::.:::::::::::::.:  :::..::::::.  .  :  :::::X.
huhoVK RFSGSGSGTDFTFTISSLQPEDIATYYCQQYDTLPLTFGGGTKV
           60         70         80         90         100
```

Figure 5

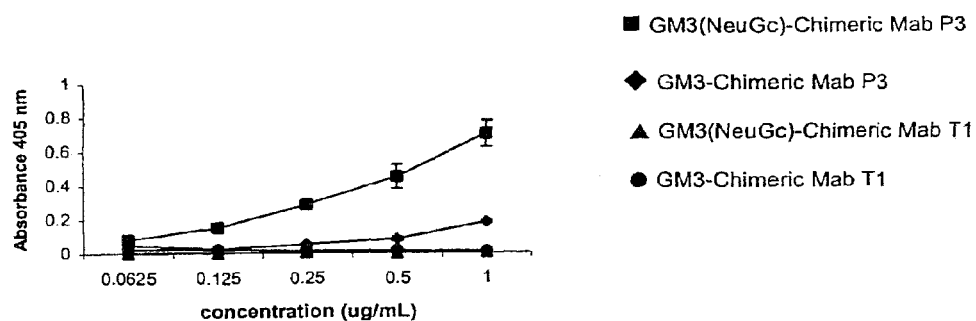

- GM3(NeuGc)-Chimeric Mab P3
- GM3-Chimeric Mab P3
- GM3(NeuGc)-Chimeric Mab T1
- GM3-Chimeric Mab T1

Figure 6

```
           1   2   3   4   5   6   7   8   9   10  11  12  13  14  15  16  17  18  19  20  21  22  23  24  25
           Q   V   Q   L   Q   Q   S   G   A   E   L   V   K   P   G   A   S   V   K   L   S   C   K   A   S
VH 1E10   CAG GTT CAG CTG CAG CAG TCT GGA GCT GAA CTG GTA AAG CCT GGG GCT TCA GTG AAG TTG TCC TGC AAG GCT TCT

_____CDR1_____
           26  27  28  29  30  31  32  33  34  35  35a 35b 36  37  38  39  40  41  42  43  44  45  46  47  48
           G   Y   T   F   T   S   Y   D   I   N               W   V   R   Q   R   P   E   Q   G   L   E   W   I
VH 1E10   GGC TAC ACC TTC ACA AGC TAT GAT ATA AAC             TGG GTG AGG CAG AGG CCT GAA CAG GGA CTT GAG TGG ATT

_____CDR2_____
           49  50  51  52  52a 52b 52c 53  54  55  56  57  58  59  60  61  62  63  64  65  66  67  68  69  70
           G   W   I   F   P               G   D   G   S   T   K   Y   N   E   K   F   K   G   K   A   T   L   T
VH 1E10   GGA TGG ATT TTT CCT             GGA GAT GGT AGT ACT AAG TAC AAT GAG AAG TTC AAG GGC AAG GCC ACA CTG ACT 71  72  73  74  75  76  77  78  79  80  81  82  82a 82b 82c 83  84  85  86  87  88  89  90  91  92
           T   D   K   S   S   S   T   A   Y   M   Q   L   S   R   L   T   S   E   D   S   A   V   Y   F   C
VH 1E10   ACA GAC AAA TCC TCC AGC ACA GCC TAC ATG CAG CTC AGC AGG CTG ACA TCT GAG GAC TCT GCT GTC TAT TTC TGT

_____CDR3_____
           93  94  95  96  97  98  99  100 100a b   c   d   101 102     103 104 105 106 107 108 109 110 111
           A   R   E   D   Y   Y   D   N   S   Y   Y   F   D   Y       W   G   Q   G   T   T   L   T   V
VH 1E10   GCA AGA GAA GAC TAC TAT GAT AAC TCC TAC TAC TTT GAC TAC     TGG GGC CAA GGC ACC ACT CTC ACA GTC
```

Figure 7

```
         1   2   3   4   5   6   7   8   9   10  11  12  13  14  15  16  17  18  19  20  21  22  23  24  25
         D   I   Q   M   T   Q   T   T   S   S   L   S   A   S   L   G   D   R   V   T   I   S   C   R   A
VklE10   GAT ATC CAG ATG ACA CAG ACT ACA TCC TCC CTG TCT GCC TCT CTG GGA GAC AGA GTC ACC ATC AGT TGC AGG GCA

___CDR1___
         26  27  27a 27b 27c 27d 27e 27f 28  29  30  31  32  33  34  35  36  37  38  39  40  41  42  43  44
         S   Q                           D   I   S   N   Y   L   N   W   Y   Q   Q   K   P   D   G   T   V
VklE10   AGT CAG ... ... ... ... ... ... GAC ATT AGC AAT TAT TTA AAC TGG TAT CAG CAG AAA CCA GAT GGA ACT GTT

___CDR2___
         45  46  47  48  49  50  51  52  53  54  55  56  57  58  59  60  61  62  63  64  65  66  67  68  69
         K   L   L   I   Y   Y   T   S   R   L   H   S   G   V   P   S   R   F   S   G   S   G   S   G   T
VklE10   AAA CTC CTG ATC TAC TAC ACA TCA AGA TTA CAC TCA GGA GTC CCA TCA AGG TTC AGT GGC AGT GGG TCT GGA ACA

___CDR3___
         70  71  72  73  74  75  76  77  78  79  80  81  82  83  84  85  86  87  88  89  90  91  92  93  94
         D   Y   S   L   T   I   S   N   L   E   Q   E   D   I   A   T   Y   F   C   Q   Q   G   N   T   L
VklE10   GAT TAT TCT CTC ACC ATT AGC AAC CTG GAG CAA GAA GAT ATT GCC ACT TAC TTT TGC CAA CAG GGT AAT ACG CTT 95  95a 95b 96  97  98  99  100 101 102 103 104 105 106 107
         P           W   T   F   G   G   T   K   L   E   I   K
VklE10   CCG         TGG ACG TTC GGT GGA GGC ACC AAG CTG GAA ATC AAA
```

Figure 8

```
                 10         20         30         40         50         60
VH1E10  QVQLQQSGAELVKPGASVKLSCKASGYTFTSYDINWVRQRPEQGLEWIGWIFPGDGSTKY
        ::X:  ::::::. ::::::::..:::::: ::  . :.:.:: :  .:::::::: :...:.  .:
huhoVH  QTQLVQSGAEVRKPGASVRVSCKASGITFIDSYIHWIRQAPGHGLEWVGWINPNSGGPNY
                 10         20         30         40         50         60

70         80         90        100        110
VH1E10  NEKFKGKATLTTDKSSSTAYMQLSRLTSEDSAVYFCARED-----YY--DNSYYFDYWGQ
        .:.:..:.:  :  : ::::::.:  :  :.::::::..::.    :V   : ::^.:  :::
huhoVH  APRFQGRVTMTRDASFSTAYMDLRSLRSDDSAVFYCAKSDPFWSDYYNFDYSYTLDVWGQ
                 70         80         90        100        110        120

VH1E10  GTTLTV
        :::.::
huhoVH  GTTVTV
```

```
           10         20         30         40         50
VK1E10  DIQMTQTTSSLSASLGDRVTISCRASQDISNYLNWYQQKPDGTVKLLIYYTSRLHSGVP
        :::::.. :::::::.::::.X:::. ::.::.::..:: . .:::: .: ::::::
huhoVK  DIQMTZSPSSLSASVGBRVTITCRASZTISSYLBWYZZKPGKAPBLLIYAASBLHSGVP
           10         20         30         40         50

60         70         80         90        100
VK1E10  SRFSGSGSGTDYSLTISNLEQEDIATYFCQQGNTLPWTFGGGTKLESK
        :::::::::::...:::.:. ...:::.:.. . : ::: ::.:X :
huhoVK  SRFSGSGSGTBFTFTISSLZPZBFATYYCZZSYSSPTTFGZGTRLZIK
         60         70         80         90        100
```

GANGLIOSIDE ASSOCIATED RECOMBINANT ANTIBODIES AND THE USE THEREOF IN THE TREATMENT OF TUMORS

PRIOR RELATED APPLICATIONS

This patent application is a divisional patent application of U.S. patent application Ser. No. 10/473,977, filed Nov. 17, 2003 now abandoned, which claims priority to PCT Patent Application PCT/CU2002/00003, filed Apr. 8, 2002 and Cuban Patent Application CU 84/2001, filed Apr. 6, 2001 and incorporates these applications in their entireties by reference thereto.

BACKGROUND

1. Field of the Invention

The present invention is related to the biotechnology field, in particular with new recombinant antibodies obtained by genetic engineering, specifically with chimeric and humanized antibodies obtained from the murine monoclonal antibody P3 (MAb P3) and its anti-idiotype murine monoclonal antibody 1E10 (MAbai 1E10).

More specifically, the invention is related with antibodies that bind to gangliosides containing N-glycolylated sialic acid, but not with the acetylated forms of the gangliosides or with neuter glycolipids. Gangliosides containing N-glycolylated sialic acid are antigens widely expressed in breast cancer and melanomas. On the other hand, the anti-tumor effect of the MAbai 1E10 has also been demonstrated in experimental models.

The present invention is also related with the pharmaceutical compositions that contain the previously described recombinant antibodies useful in the diagnosis and therapy of cancer, particularly breast cancer and melanomas.

2. Discussion of the Prior Art

Gangliosides are glycosphingolipids that contain sialic acid and they are present in the plasmatic membrane of cells in vertebrates (Stults et al. (1989): Glycosphingolipids: structure, biological source and properties, Methods Enzymology, 179:167-214). Some of these molecules have been reported in the literature as tumor-associated antigens or tumor markers (Hakomori et al. (1991): Possible functions of tumor associated carbohydrate antigens, Curr. Opin. Immunol., 3: 646-653). For that reason the use of anti-ganglioside antibodies has been described as useful in the diagnosis and therapy of cancer (Hougton et al. (1985): Mouse monoclonal antibody IgG3 antibody detecting GD3 ganglioside: to phase I trial in patients with malignant melanoma, PNAS USA, 82:1242-1246; Zhang et al. (1997): Selection of carbohydrate tumor antigens as targets for immune attack using immunohistochemistry. I. Focus on gangliosides, Int. J. Cancer, 73: 42-49).

The sialic acids more frequently expressed in animals are N-acetyl (NeuAc) and N-glycolyl (NeuGc) (Corfield et al. (1982): Occurrence of sialic acids, Cell. Biol. Monogr., 10: 5-50). Generally, NeuGc is not expressed in normal human and chickens tissues, but it is broadly distributed in other vertebrates (Leeden and Yu, (1976): Chemistry and analysis of sialic acid. In: Biological Role of Sialic Acid. Rosemberg A and Shengtrund C L (Eds). Plenum Press, New York, 1-48; Kawai et al. (1991): Quantitative determination of N-glycolylneuraminic acid expression in human cancerous tissues and avian lymphoma cell lines as a tumor associated sialic acid by gas chromatography-mass spectrometry, Cancer Research, 51: 1242-1246). However, there are reports that show that anti-NeuGc antibodies recognize some human tumors and tumor cell lines (Higashi et al. (1988): Detection of gangliosides as N-glycolylneuraminic acid specific tumor-associated Hanganutziu-Deicher antigen in human retinoblastoma cells, Jpn. J. Cancer Res., 79: 952-956; Fukui et al. (1989): Detection of glycoproteins as tumor associated Hanganutziu-Deicher antigen in human gastric cancer cell line, NUGC4, Biochem. Biophys. Res. Commun., 160: 1149-1154). Increased levels of GM3 (NeuGc) gangliosides have been found in human breast cancer (Marquina et al. (1996): Gangliosides expressed in human breast cancer, Cancer Research, 1996; 56: 5165-5171), and this result makes attractive the use of this molecule as a target for cancer therapy.

The monoclonal antibody (Mab) P3, produced by the cell line deposited with accession number ECACC 94113026 (European Patent EP 0 657 471 B1), is a murine monoclonal antibody with IgM isotype. Mab P3 was obtained when fusing murine splenocytes from a BALB/c mouse immunized with liposomes containing GM3(NeuGc) and tetanic toxoid with the cell line P3-X63-Ag8.653, which is a murine myeloma. This Mab P3 reacts strongly with N-glycolylated sialic acid-containing gangliosides but not with the acetylated forms of the gangliosides, nor with the neuter glycolipids. It was demonstrated by immunocytochemical and immunohistochemical studies carried out with cell lines and tissues from benign and neoplasic tumors that the Mab P3 recognizes breast cancer (Vzquez et al. (1995): Generation of a murine monoclonal antibody specific for N-glycolylneuraminic acid-containing gangliosides that also recognizes sulfated glycolipids, Hybridoma, 14: 551-556) and melanoma.

The Mab P3 induced an anti-idiotypic immune response (Ab2) in BALB/c mice (syngeneic model), even without adjuvant and carrier protein (Vazquez et al. (1998): Syngeneic anti-idiotypic monoclonal antibodies to an anti-NeuGc-containing ganglioside monoclonal antibody, Hybridoma, 17: 527-534). A role for the electronegative groups, sialic acid (for gangliosides) or $SO_3$— (for sulfatides), in the recognition properties of this antibody was suggested by immunochemical analysis (Moreno et al. (1998): Delineation of epitope recognized by an antibody specific for N-glycolylneuraminic acid-containing gangliosides, Glycobiology, 8: 695-705).

The anti-idiotypic Mab 1E10 (Mabai 1E10) of IgG1 subtype was obtained from a BALB/c mouse immunized with the Mab P3 coupled to KLH (U.S. Pat. No. 6,063,379, cell line deposited under accession number ECACC 97112901). Mabai 1E10 specifically recognized MAb P3 and did not bind other IgM anti-ganglioside antibodies. Moreover, Mabai 1E10 inhibited the specific binding of Mab P3 to GM3 (NeuGc) and to the ductal breast carcinoma-derived cell line MDA-MB-435, which is positive for Mab P3 binding. The MAbai 1E10 induced a strong immune response of Ab3 antibodies when mice from syngeneic or alogenic models were immunized. These Ab3 antibodies did not exhibit the same specificity as the Mab P3 even though they carry idiotopes similar to those carried by the Ab1 antibody (Vazquez et al. (1998): Syngeneic anti-idiotypic monoclonal antibodies to an anti-NeuGc-containing ganglioside monoclonal antibody, Hybridoma, 17: 527-534). MAbai 1E10 induced a strong antitumor effect in syngeneic as well as alogenic mice. The growth of the mammary carcinoma cell line F311 was significantly reduced by repeated doses of KLH-coupled MAbai 1E10 in Freund's adjuvant when BALB/c mice were vaccinated. Also the number of spontaneous lung metastasis was reduced after the vaccination. Intravenous administration of the MAbai 1E10 to C57BLU6 mice, 10 to 14 days after the intravenous inoculation of B16 melanoma cells, caused a dramatic reduction of the number of lung metastases when compared with mice treated with an irrelevant IgG. These results suggest that more than one anti tumor effect mechanism is triggered (Vazquez et al. (2000): Anti tumor properties of an anti-idiotypic monoclonal antibody in relation to N-glycolyl-containing gangliosides, Oncol. Rep., 7: 751-756, 2000).

Even though hybridoma technology has been developed for 15 years (Koehler y Milstein (1975): Continuous cultures of fused cells secreting antibody of predefined specificity, Nature, 256: 495497) and monoclonal antibodies are still very useful in diagnosis as well as research, they have not demonstrated their therapeutic effectiveness in humans. This has been mainly due to their short half-life in blood, to the human anti-mouse antibody immune response (HAMA response), and also because murine effector functions fail for the human immune system.

Genetic engineering technology has revolutionized MAb potential, since by manipulating immunoglobulin genes it is possible to obtain modified antibodies with reduced antigenicity, as well as to improve their effector functions when used in the treatment or diagnosis of certain pathologies. Methods for reducing immunoglobulin immunogenicity have as essential object to diminish the differences between the murine antibody and a human immunoglobulin, without altering the antigen recognition specificity (Morrison y Oi (1989): Genetically engineered antibody molecules, Adv Immunol., 44: 65-92).

Recently, several methods have been developed to humanize murine or rat antibodies, thus reducing the xenogenic immune response against foreign proteins when they are injected into humans. One of the first approaches to reduce the antigenicity were chimeric antibodies, in which the variable domains of the murine protein are inserted in constant domains of human molecules that exhibit the same specificity but reduced immunogenicity compared to their murine counterparts. Additionally, human effector functions are preserved by chimeric antibodies (Morrison et al. (1984): Chimeric human antibody molecules: Mouse antigen-binding domains with human constant region domains, PNAS USA, 81: 6851-6855). Even when chimeric antibodies have the same specificity as their murine counterpart, an immune response to the rodent variable regions is frequently observed.

In an attempt to further reduce the immunogenicity of chimeric antibodies, only the CDRs from the rodent monoclonal antibody have been grafted onto human framework regions and this hybrid variable region has been expressed with human constant regions (Jones et al. (1986): Replacing the complementary-determining regions in a human antibody with those from a mouse, Nature 321: 522-524; Verhoeyen et al. (1988): Reshaping human antibodies: grafting an antilysozyme activity, Science 239, 1534-1536). However, this approach has several shortcomings: frequently the resulting antibody has decreased affinity and a number of framework residues must be mutated back to the corresponding murine ones to restore binding (Rietchmann et al. (1988): Reshaping human antibodies for therapy, Nature, 332: 323-327; Queen et al. (1989): A humanized antibody that binds to the interleukin 2 receptor, PNAS USA, 86: 10029-10033; Tempest et al. (1991): Reshaping a human monoclonal antibody to inhibit human respiratory syncytial virus infection in vivo, Biotechnology, 9: 266-272). In addition, persisting immunogenicity is frequently observed in the CDR-grafted antibodies.

Mateo and collaborators (U.S. Pat. No. 5,712,120) have described a procedure for reducing immunogenicity of murine antibodies. According to the method, the modifications are restricted to the variable domains and specifically to the murine FRs of chimeric antibodies. Moreover, the replacements are only carried out in those regions of the FRs that have amphipatic sequences and therefore they are potential epitopes recognized by T cells.

The method comprises judicious replacement of a few amino acid residues, located in the potential immunogenic epitopes by the corresponding residues from the most homologous human sequence. Those amino acids that are mainly responsible for canonical structures, as well as the residues in the immediate neighborhood of the CDRs or in the Vernier zone must be retained.

The resulting antibody retains its antigen binding specificity and is less immunogenic than either its murine or chimeric predecessor (Mateo et al. (2000): Removal of T cell epitopes from genetically engineered antibodies: Production of modified immunoglobulins with reduced immunogenicity, Hybridoma 19: 463-71). These properties increase its therapeutic usefulness. Using this new procedure, only few mutations, and of course less genetic manipulations, have to be done.

DETAILED DESCRIPTION OF THE INVENTION

The present invention is related to recombinant antibodies, obtained by genetic engineering technology. Specifically, the invention is related to a chimeric antibody derived from the murine monoclonal antibody P3, produced by hybridoma cell line with deposit number ECACC 94113026. MAB P3 recognizes an antigen expressed in breast tumor cells and melanomas. The MAb P3 is characterized by the following sequences of the hypervariable regions (CDRs) of the heavy and light chains:

```
Heavy Chain
                                    (SEQ ID NO: 1)
CDR1: RYSVH (SEQ ID NO: 2)
CDR2: MIWGGGSTDYNSALKS (SEQ ID NO: 3)
CDR3: SGVREGRAQAWFAY Light Chain
                                    (SEQ ID NO: 4)
CDR1: KASQDVSTAVA (SEQ ID NO: 5)
CDR2: SASYRYT (SEQ ID NO: 6)
CDR3: QQHYSTPWT
```

Preferably, the FRs sequences of the heavy and light chain are the following:

```
Heavy Chain
                                    (SEQ ID NO: 7)
FR1: QVQLKESGPGLVAPSQSLSITCTVSGFSLS (SEQ ID NO: 8)
FR2: WVRQPPGKGLEWLG (SEQ ID NO: 9)
FR3: RLSISKDNSKSQVFLKMNSLQTDDTAMYYCAR (SEQ ID NO: 10)
FR4: WGQGTLV Light Chain
                                    (SEQ ID NO: 11)
FR1: DIVMTQSHKFMSTSVGDRVSITC
```

```
                                            (SEQ ID NO: 12)
FR2:  WYQQKPGQSPKLLIY (SEQ ID NO: 13)
FR3:  GVPDRFTGSGSGTDFTFTISSVQAEDLAVYYC (SEQ ID NO: 14)
FR4:  FGGGTKL
```

In a preferred embodiment, the chimeric antibody of the present invention contains the constant region of human IgG1 heavy chain and the constant region of human Ck light chain. In another aspect, the present invention is related with a humanized antibody derived from the Mab P3 produced by the hybridoma cell line with deposit number ECACC 94113026, characterized in that it contains the constant region of human IgG1 heavy chain and the constant region of human Ck light chain and the FRs regions of the light chain contain any of the following point mutations:

```
Light Chain:
Position 8  in SEQ ID NO: 11: His by Pro

Position 9  in SEQ ID NO: 11: Lys by Ser

Position 10 in SEQ ID NO: 11: Phe by Ser

Position 11 in SEQ ID NO: 11: Met by Leu

Position 13 in SEQ ID NO: 11: Thr by Ala
```

In another aspect, the invention is related with a chimeric antibody derived from the murine monoclonal antibody 1E10 produced by the hybridoma cell line with deposit number ECACC 97112901 and it is an antiidiotype antibody which recognizes the MAb P3. The MAbai 1E10 is characterized by the following sequences of the hypervariable regions (CDRs) of the heavy and light chains:

```
            Heavy chain
                                            (SEQ ID NO: 15)
            CDR1:  SYDIN (SEQ ID NO: 16)
            CDR2:  WIFPGDGSTKYNEKFKG (SEQ ID NO: 17)
            CDR3:  EDYYDNSYYFDY Light chain
                                            (SEQ ID NO: 18)
            CDR1:  RASQDISNYLN (SEQ ID NO: 19)
            CDR2:  YTSRLHSG (SEQ ID NO: 20)
            CDR3:  QQGNTLPWT
```

Preferably, the FRs sequences of the heavy and light chains are the following:

```
            Heavy chain
                                            (SEQ ID NO: 21)
            FR1:  QVQLQQSGAELVKPGASVKLSCKASGYTFT (SEQ ID NO: 22)
            FR2:  WVRQRPEQGLEWIG (SEQ ID NO: 23)
            FR3:  KATLTTDKSSSTAYMQLSRLTSEDSAVYFCAR
```

```
                                            (SEQ ID NO: 24)
            FR4:  WGQGTTLTV

Light chain
                                            (SEQ ID NO: 25)
            FR1:  DIQMTQTTSSLSASLGDRVTISC (SEQ ID NO: 26)
            FR2:  WYQQKPDGTVKLLIY (SEQ ID NO: 27)
            FR3:  VPSRFSGSGSGTDYSLTISNLEQEDIATYFC (SEQ ID NO: 28)
            FR4:  FGGGTKLESK
```

In a preferred embodiment, the chimeric antibody of the present invention contains the constant region of human IgG1 heavy chain and the constant region of human Ck light chain.

In another aspect, the present invention is related with a humanized antibody derived from the Mab 1E10 produced by the hybridoma cell line with deposit number ECACC 97112901, characterized in that it contains the constant region of human IgG1 heavy chain and the constant region of human Ck light chain and the FRs regions of the heavy and light chains contain any of the following point mutations:

```
Light Chain:
Position 7  in SEQ ID NO: 25: Thr by Ser

Position 8  in SEQ ID NO: 25: Thr by Pro

Position 15 in SEQ ID NO: 25: Leu by Val

Heavy Chain:
Position 5  in SEQ ID NO: 21: Gln by Val

Position 5  in SEQ ID NO: 22: Arg by Ala

Position 7  in SEQ ID NO: 22: Glu by Gly

Position 21 in SEQ ID NO: 23: Thr by Arg
```

Position 21 in SEQ ID NO: 23: Thr by Arg

In another aspect, the present invention is related to the cell lines that express the described chimeric and humanized antibodies; additionally the invention is related to pharmaceutical compositions comprising the described antibodies.

Preferably it is related with pharmaceutical compositions for the treatment of breast, lung, digestive system, urogenital system, melanomas, sarcomas and neuroectodermic tumors, their metastases and relapses, comprising the described antibodies and an appropriate exicipient.

In another representation of the present invention, the pharmaceutical compositions can be used for the in vivo localization and diagnosis of breast, lung, digestive system, urogenital system, melanomas, sarcomas and neuroectodrmico tumors, their metastases and relapses, comprising the described antibodies.

cDNA Synthesis and Gene Amplification by PCR (Polymerase chain reaction) of the Variable Region of MAb P3 and Mabai 1E10.

Cytoplasmic RNA was extracted from about $10^6$ P3 hybridoma cells (murine IgM MAb that recognizes GM3 N-glycolylated gangliosides) or 1E10 (antiidiotype anti-P3 antibody). The RNA was extracted using the reagent TRIZOL® (GIBCO® BRL, Grand Island, N.Y.), according to the manufacturer's instructions.

The cDNA synthesis reaction was carried out mixing 5 µg of the RNA, 25 pmoles of Vh (complementary to the constant region of murine IgM for VHP3, and with the constant region of murine IgG1 for VH 1E10) or Vk (complementary to constant murine kappa region for both antibodies), 2.5 mM of each dNTP, 50 mM Tris-Hcl pH 7.5, 75 mM KCl, 10 mM DTT, 8 mM MgCl2 and 15 units of RNAse inhibitor in a 50 µl reaction mixture. It was heated at 70° C. for 10 minutes and slowly cooled up to 37° C. Then, 100 units of MLV reverse transcriptase enzyme were added and incubation at 42° C. continued for one hour.

The VK and VH variable region cDNAs were amplified by PCR. Briefly, 5 µl cDNA of VH or VK were mixed with 25 pmoles of specific primers, 2.5 mM of each dNTP, 5 µl constituents of 10× buffer Taq DNA polymerase and 1 unit of this enzyme. The samples were subjected to 25 thermal cycles at 94° C., 30 sec; 50° C., 30 sec; 72° C., 1 min, and a last incubation for 5 minutes at 72° C.

Cloning and Sequencing of Amplified cDNA

The PCR products of VH and VK (of the P3 and of the 1E10, respectively) were cloned into TA vector (TA Cloning kit. Promega, USA). The resulting clones were sequenced by the dideoxy method using T7 DNA Polymerase (T7 sequencing kit, Pharmacia, Sweden).

Construction of Chimeric Genes

The VH and VK genes were excised from TA vectors by enzymatic digestion and were cloned into the respective expression vectors (Coloma et al. (1992): Novel vectors for the expression of antibody molecules using variable regions generated by polymerase chain reaction, J. Immunol. Meth., 152: 89-104).

The VH genes were excised from the TA vector by enzymatic digestion with EcoRV and NheI and cloned into an expression vector (PAH 4604) that includes a human IgG1 variable region and the histidinol resistance gene. The resultant constructions were P3VH-PAH4604 and 1E10VH-PAH4604. The VK genes were excised from TA vector by enzymatic digestion with EcoRV and SalI and cloned into an expression vector (PAG4622). This vector included mycophenolic acid resistance gene and the human kappa constant region. The resultant constructions were P3VK-PAG4622 and 1E10VK-PAG4622.

Expression of Chimeric Antibodies Obtained from Mab P3 and MAbai 1E10.

NS-0 cells were electroporated with 10 µg of P3VK-PAG4622 or 1E10VK-PAG4622, and clones expressing human kappa light chains were transfected with 10 µg of P3VH-PAH4604 or 1E10VH-PAH4604.

The DNAs were linearized by digestion with PvuI enzyme, precipitated with ethanol and dissolved in 50 µl of PBS. Approximately $10^7$ cells were harvested by centrifugation and re-suspended in 0.5 ml of PBS together with the digested DNA in an electroporation cuvette. After 10 minutes on ice, the cells were given a pulse of 200 volts and 960 µF and left in ice for further 10 minutes. The cells were distributed into a 96 well plate with D'MEM F12 supplemented with 10% fetal calf serum. Two or four days later, selective medium (D'MEM F12 with mycophenolic acid 0.45 µg/mL or histidinol 10 mM, respectively) is added. Transfected clones were visible to the naked eye 14 days later.

The presence of human antibody in the medium of the wells containing transfected clones was measured by ELISA. Microtiter plate wells were coated with goat anti-human kappa light chain antibodies (for human kappa chain producing clones) or anti-human IgG antibodies (gamma chain specific) (for the complete antibody producing clones). After washing with PBST (saline phosphate buffered solution containing 0.05% Tween 20), diluted culture medium of the wells containing transfectants was added to each microtiter well for one hour at 37° C. The wells were washed with PBS-T, spicy radish peroxidase-conjugated goat anti-human kappa light chain or alkaline phosphatase-conjugated goat anti-human IgG (gamma chain specific) was added and incubation took place at 37° C. for one hour. The wells were washed with PBS-T and substrate buffer was added containing o-phenylendiamine or p-nitrophenylphosphate, respectively. After half an hour, the absorbance was measured at 492 or 405 nm, respectively.

Construction of the Humanized Antibodies P3hu and 1E10 hu by Humanization of T Cell Epitopes. Prediction of T Cell Epitopes The sequences of P3 and 1E10 variable domains were analyzed with the algorithm AMPHI (Margalit et al. (1987): Prediction of immunodominant helper T cell antigenic sites from the primary sequence, J. Immunol., 138: 2213-2229). It searched helical amphipatic segments, with 7 or 11 amino acid residues, which have been associated with T immunogenicity. The program SOHHA also predicted helical hydrophobic segments (Elliot et al. (1987). An hypothesis on the binding of an amphipatic, alpha helical sequence in li to the desotope of class II antigen, J. Immunol., 138: 2949-2952). Both algorithms predicted which segments from variable region sequences of antibodies P3 and 1E10 could be presented to T-helper cells in the context of MHC class 11 molecules.

Homology Analysis with Human Immunoglobulins.

The amino acid sequences of murine variable regions were compared with the immunoglobulin sequences included in the GeneBank and EMBL database (available in Internet). The most homologous human variable region sequence was determined for each antibody. Software PC-TWO HIBIO PROSIS 06-00 (Hitachi) was used for sequence homology searching.

Analysis for the Immunogenicity Reduction.

The aim of the method is to reduce immunogenicity, breaking or humanizing potential immunogenic T epitopes with a minimum of changes. The method comprises judicious replacement of few amino acid residues, located into helical amphipatic segments. The amino acids which are mainly responsible for canonical structures, as well as the residues in the immediate neighborhood of the CDRs or into the Vernier zone, must be retained.

According to the method, murine variable region sequences were compared with the most homologous human sequence and amino acid residues that differ between the murine MAb and the most homologous human sequence were identified, only taking into account those residues inside the FRs (Kabat (1991), Sequences of proteins of immunological interest, Fifth Edition, National Institute of Health). The previously defined residues were replaced by those residues present in the most homologous human sequence. Replacements were made by directed mutagenesis techniques.

Residues involved in three-dimensional structure of the binding site were not mutated; it could affect antigen recognition. Additional information about the influence of the replacements in the tertiary structure can be obtained by molecular modeling of the antigen binding site.

The presence of proline residues in the helical amphipatic segment and the fact that a certain murine residue does not appear in the same position in the most homologous human sequence but is frequent in other human immunoglobulins must be kept in mind. For that reason, there is not a unique ensemble of murine amino acids to be replaced in the frameworks. It is possible to obtain different versions of the modified antibody with different number of replacements. The mutations were carried out by overlapping PCRs.

Cloning and Expressing Humanized Antibodies P3hu and 1E10hu.

The genetic constructions corresponding to the P3hu and 1E10hu, were cloned in expression vectors following the method described for the chimeric antibodies. The resultant constructions were P3VKhu-PAG4622 or 1E10Vkhu-PAG4622 and P3VHhu-PAH4604 and 1E10VHhu-PAH4604. They were transfected into NS-0 cells following the protocol described previously for chimeric antibodies.

Purification of the Recombinant Antibodies.

The recombinant antibodies were purified by affinity chromatography using protein A (Pharmacia, Upsala, Sweden).

Biological Activity.

The biological activity of the recombinant antibodies was tested by their specific binding to antigen as measured by ELISA.

For recombinant MAb P3, microtiter plates were coated with GM3(NeuGc) ganglioside in methanol. After drying for one hour, unspecific binding was blocked by incubating for one hour at 37° C. with bovine sera albumin (BSA) 1% in Tris-HCl buffer. The wells were washed with PBS and incubated for 1 hour at 37° C. with purified recombinant Mab P3. The wells were washed with tris-HCl and incubated at 37° C. for one hour with goat anti-human antibody conjugated with alkaline phosphatase. Finally, the wells were washed and substrate buffer containing p-nitrophenylphosphate was added. After half an hour, absorbance was measured at 405 or 492 nm, respectively.

For recombinant MAbai 1E10, the ELISA assay was similar, except that wells were coated with Mab P3 and washing steps were made with PBS-0.05% Tween 20.

EXAMPLES

In the following examples all the enzymes used, as well as reagents and materials, were obtained from commercial sources unless otherwise specified.

Example 1

Obtaining of Chimeric MAb P3

The cDNA synthesis was obtained by a reaction with reverse transcriptase enzyme, starting with RNA from the hybridoma producing Mab P3, as described previously. The sequence of the specific primers used in this reaction is shown:

```
For VH:
                                        (SEQ ID NO: 29)
5' AGGTCTAGAA(CT)CTCCACACAC AGG(AG)(AG)CCAGTGGATA
GAC 3'

For VK:
                                        (SEQ ID NO: 30)
5' GCGTCTAGAACTGGATGGTGGGAAGATGG 3'
``` cDNA VHP3 and cDNA VKP3 were amplified by PCR using Taq Polymerase and specific primers. The restriction sites included in the primers were ECORV/NHEI, for VH and ECORV/SALI for VK. The primer sequences used were the following:

```
For VH:
Primer 1 (signal peptide):
                                        (SEQ ID NO: 31)
5'GGGGATATCCACCATGG(AG)ATG(CG) AGCTG(TG)GT(CA)AT
(CG)CTCTT 3'

Primer 2 (CH1):
                                        (SEQ ID NO: 32)
5' GGGGCTAGCTGCAGAGACAGTGACCAGAGT 3'

For VK:
Primer 1 (signal peptide):
                                        (SEQ ID NO: 33)
5' GGGGATATCCACCATGGAG(TA)CAC A(GT)(TA)CTCAGGTCTTT
(GA)T 3'

Primer 2 (Ck):
                                        (SEQ ID NO: 34)
5' AGCGTCGACTTACGTTT(TG)ATTTCCA(GA)CTT(GT)GTCCC 3'
```

PCR products were cloned into TA vector (TA cloning kit, Invitrogen). Twelve independent clones were sequenced by the dideoxy method using T7 DNA Pol (Pharmacia). The most homologous sequence groups for VHP3 and VKP3 was determined by homology search analysis. VHP3 and VKP3 sequences (FIGS. 1 and 2) have high homology with groups IB and V, respectively, according to Kabat's classification.

After digestion with the restriction enzymes ECORV and NHEI for VHP3 and with ECORV and SALI for VKP3, they were cloned in the expression vectors PAH4604 and PAG4622 (for VH and VK, respectively), both previously digested with the same enzymes. These expression vectors were donated by Sherie Morrison (UCLA, Calif., USA), and they are suitable for immunoglobulin expression in mammalian cells. Vector PAH 4604 includes the human IgG1 constant region and vector PAG 4622 the human Ck (Coloma et al. (1992): Novel vectors for the expression of antibody molecules using variable regions generated by polymerase chain reaction, J. Immunol. Meth., 152: 89-104). The resultant constructs were P3VH-PAH4604 and P3VK-PAG4622.

NS-0 cells were transfected with 10 µg of P3VK-PAG4622, and the clone expressing light chain was transfected with 10 µg P3VH-PAH4604. In both cases DNA was linearized with Pvul, ethanol precipitated and dissolved in 50 µl of PBS before transfection.

Approximately $10^7$ cells were harvested by centrifugation and resupended in 0.5 ml of PBS together with the digested DNA in an electroporation cuvette. After 10 minutes on ice, the cells were given a pulse of 200 volts and 960 µF and left in ice for further 10 minutes. The cells were distributed into a 96 well plate with D'MEM F12 supplemented with 10% fetal calf serum. Two or four days later, selective medium (D'MEM F12 with mycophenolic acid 0.45 µg/mL or histidinol 10 mM, respectively) is added. Transfected clones were visible to the naked eye 14 days later.

The presence of human antibody in the medium of wells containing transfected clones was measured by ELISA. Microtiter plate wells were coated with goat anti-human kappa light chain antibody (for human kappa chain producing clones) or anti-human IgG antibody (gamma chain specific) (for the complete antibody producing clones). After washing with PBST (saline phosphate buffered solution containing 0.05% Tween 20), diluted culture medium of the wells containing transfectants was added to each Microtiter well for one hour at 37° C. The wells were washed with PBS-T, spicy radish peroxidase-conjugated goat anti-human kappa light chain or alkaline phosphatase-conjugated goat anti-human IgG (gamma chain specific) was added, and incubation took place at room temperature for one hour. The wells were washed with PBS-T and substrate buffer containing o-phenylendiamine or p-nitrophenylphosphate, respectively, was added. After half an hour, absorbance was measured at 492 or 405 nm, respectively.

Example 2

Obtaining Different Versions of the Humanized Antibody P3

Murine VHP3 and VKP3 sequences (FIGS. 1 and 2) were compared with human sequences. FIGS. 3 and 4 show the most homologous human sequences. Helical amphipatic regions or potential T cell epitopes were searched on murine P3 variable region sequences and, according to the method, a judicious strategy for amino acid replacements was established in order to break or humanize potential T cell epitopes inside the murine sequences.

The analysis on VHP3 rendered (FIG. 3) 2 amphipatic segments; the first one embraces CDR1, FR2 and some residues of the CDR2, while the second one embraces the end of FR3 and CDR3. The main differences of the murine sequence in comparison with the most homologous human sequence were found in CDRs or in residues involved in the three dimensional structure of the binding site. For that reason it was decided not to replace any amino acids in murine VHP3.

The analysis for VKP3 also rendered 2 amphipatic segments (FIG. 4); the first segment embraces FR1, while the second one embraces CDR2 and some residues of FR3. It was decided to replace residues at positions 8, 9, 10, 11 and 13 by residues at the same positions in the most homologous human sequence. The amino acids His, Lys, Phe, Met and Thr were replaced by Pro, Ser, Ser, Leu, and Ala, respectively. The replacements were made by overlapping PCR (Kammann et al. (1989) Rapid insertional mutagenesis of DNA by polymerase chain reaction (PCR), Nucleic Acids Res., 17: 5404) using primers 1, 2, 3 and 4, whose sequences are the following:

```
                                         (SEQ ID NO: 35)
Primer 1: 5' ATGACCCAGTCTCCTTCTTCTCTTTCCGCGTCAGTAG
GAGAC 3'

(SEQ ID NO: 36)
Primer 2: 5' AGCGTCGACTTACGTTT(TG)ATTTCCA(GA)CT-
T(GT)GTCCC 3'

(SEQ ID NO: 37)
Primer 3: 5' GTCTCCTACTGACGCGGAAAGAGA-AGAAGGAGACTG
GGTCAT 3'

(SEQ ID NO: 38)
Primer 4: 5'GGGGATATCCACCATGGAG(TA)CACA(GT)(TA)CTC
AGGTCTTT(GA)T 3'
```

The point mutations were verified by sequencing. The resulting construct was P3Vkhu and it was cloned in PAG 4622 expression vector. The resulting construct was P3VKhu-PAG4622.

To express the humanized antibody P3, NS-0 cells were transfected with P3VH-PAH4604 and P3VKhu-PAG4622. P3hu antibody was transfected following the same electroporation and detection procedure described previously for the chimeric antibodies.

Example 3

Biological Activity of Chimeric MAb P3

The biological activity of the chimeric Mab P3 was tested by its specific binding to antigen as measured by ELISA.

For recombinant MAb P3, microtiter plates were coated with GM3(NeuGc) ganglioside in methanol. After drying one hour at 37° C., unspecific binding was blocked by incubating with 1% bovine sera albumin (BSA) in Tris-HCl buffer for one hour at 37° C. The wells were washed with PBS and incubated for 1 hour at 37° C. with purified recombinant Mab P3. The wells were washed with tris-HCl and incubated with goat anti-human antibody conjugated with alkaline phosphatase at 37° C. for one hour. Finally, the wells were washed with Tris-HCl and substrate buffer containing p-nitrophenylphosphate was added. After half an hour, absorbance was measured at 405 nm.

Chimeric Mab Ti was used as negative control.

FIG. 5 shows the specific binding of chimeric Mab P3 to the antigen.

Example 4

Obtaining of Chimeric MAb 1E10

The cDNA synthesis was obtained by a reaction with reverse transcriptase enzyme, starting with RNA from the hybridoma producing Mab 1E10, as described previously. The sequence of the specific primers used in this reaction is shown below:

```
For VH:
                                         (SEQ ID NO: 39)
    5'GGGGCTAGCTGAGGAGACTGTGAGAGTGGT 3'

For VK:
                                         (SEQ ID NO: 40)
    5'GCGTCTAGAACTGGATGGTGGGAAGATGGA 3'
``` cDNA VH1E10 and cDNA VK1E10 were amplified by PCR using Taq Pol and specific primers.

```
For VH:
                                         (SEQ ID NO: 41)
Primer 1 (signal peptide): 5'GGGGATATCCACCATGG(AG)
ATG-(CG)AGCTG(TG)GT(CA)AT(CG)CTCTT 3'

(SEQ ID NO: 42)
Primer 2 (CH1): 5' GGGGCTAGCTGAGGAGACTGTGAGAGTGG
T 3'

For VK:
                                         (SEQ ID NO: 43)
Primer 1 (signal peptide): 5'GGGGTTAACCACCATGAGG
(GT)C-CCC(AT)GCTCAG(CT)T(CT)CT(TG)GG(GA)3'

(SEQ ID NO: 44)
Primer 2 (Ck): 5'AGCGTCGACTTACGTTT(TG)ATTTCCA(GA)C
TT(GT)GTCCC3'
```

PCR products were cloned into TA vector (TA cloning kit, Invitrogen). Twelve independent clones were sequenced (FIGS. 7 and 8) by the dideoxy method using T7 DNA Pol (Pharmacia). The most homologous sequence group for VHIE10 and VK1E10 was determined by homology search analysis. VH1E10 and VK1E10 sequences have high homology with groups miscellaneous and V, respectively, according to Kabat's classification.

After digestion with the restriction enzymes ECORV and NHEI for VH1E10 and with HincII and SALI for VKIE10, they were cloned in the expression vectors PAH4604 and PAG4622 (for VH and VK, respectively), both previously digested with appropriate enzymes. These expression vectors were donated by Sherie Morrison (UCLA, Calif., USA), and they are suitable for immunoglobulin expression in mammalian cells. Vector PAH 4604 includes the human IgG1 constant region and vector PAG 4622 the human Ck (Coloma et al. (1992): Novel vectors for the expression of antibody molecules using variable regions generated by polymerase chain reaction, J. Immunol. Meth., 152: 89-104). The resultant constructs were 1E10VH-PAH4604 and 1E10VK-PAG4622.

NS-0 cells were transfected with 10 µg of 1E10VK-PAG4622, and a clone expressing light chain was transfected with 10 µg 1E10VH-PAH4604. In both cases DNA was linearized with PvuI, ethanol precipitated and dissolved in 50 µl of PBS before transfection.

Approximately $10^7$ cells were harvested by centrifugation and re-suspended in 0.5 ml of PBS together with the digested DNA in an electroporation cuvette. After 10 minutes on ice, the cells were given a pulse of 200 volts and 960 .µF. and left in ice for further 10 minutes. The cells were distributed into a 96 well plate with D'MEM F12 supplemented with 10% fetal calf serum. Two or four days later, selective medium (D'MEM F12 with mycophenolic acid 0.45 µg/mL or histidinol 10 mM, respectively) is added. Transfected clones were visible to the naked eye 14 days later.

The presence of human antibody in the medium of wells containing transfected clones was measured by ELISA. Microtiter plate wells were coated with goat anti-human kappa light chain antibody (for human kappa chain producing clones) or anti-human IgG antibody (gamma chain specific) (for the complete antibody producing clones). After washing with PBST (phosphate buffered saline containing 0.05% Tween 20), diluted culture medium of the wells containing transfectants was added to each Microtiter well for one hour at 37° C. The wells were washed with PBS-T, spicy radish peroxidase-conjugated goat anti-human kappa light chain or alkaline phosphatase-conjugated goat anti-human IgG (gamma chain specific) was added, and incubation took place at room temperature for one hour. The wells were washed with PBS-T and substrate buffer containing o-phenylendiamine or p-nitrophenylphosphate, respectively, was added. After half an hour, absorbance was measured at 492 or 405 nm, respectively.

Example 5

Obtaining Different Versions of the Humanized Antibody 1E10

Murine VH1E10 VK1E10 sequences (FIGS. 6 and 7) were compared with human sequences. FIGS. 8 and 9 shown the most homologous human sequences. Helical amphipatic regions or potential T cell epitopes were searched on murine 1E10 variable region sequences and, according to the method, a judicious strategy for amino acid replacements was established in order to break or humanize potential T cell epitopes inside the murine sequences The analysis on VH1E10 rendered (FIG. 8) 3 amphipatic segments; the first one embraces FR1, the second one embraces FR2, and the third one embraces FR3. It was decided to replace residues at positions 5, 40, 42 and 87 (83 according to Kabat's numbering) by residues at the same position in the most homologous human sequence. The amino acids Gln, Arg, Glu were replaced by Val, Ala, Gly and Arg, respectively.

The replacements were made by overlapping PCR (Kammann et al. (1989) Rapid insertional mutagenesis of DNA by polymerase chain reaction (PCR), Nucleic Acids Res., 17: 5404) using different sets of primers.

Primers for mutation at position 5, of the heavy chain were 1, 2, 3 and 4 whose sequences are the following:

```
                                          (SEQ ID NO: 45)
Primer 1: 5' CAGGTTCAGCTGGTGCAGTCTGGAGCT 3'

(SEQ ID NO: 46)
Primer 2: 5' GGGGCTAGCTGAGGAGACTGTGAGAGTGGT 3'

(SEQ ID NO: 47)
Primer 3: 5' AGCTCCAGACTGCACCAGCTGAACCTG 3'

(SEQ ID NO: 48)
Primer 4: 5'GGGGATATCCACCATGG(AG)ATG(CG)AGCTG
          (TG)GT(CA)AT(CG)CTCTT 3'
```

After checking the point mutation at position 5 by sequencing, mutations at positions 40 and 42 were introduced.

Primer for mutations at positions 40 and 42 of the heavy chain:

```
                                          (SEQ ID NO: 49)
Primer 1: 5' TGGGTGAGGCAGGCGCCTGGGCAGGGACTTGAG 3'

(SEQ ID NO: 50)
Primer 2: 5' GGGGCTAGCTGAGGAGACTGTGAGAGTGGT 3'

(SEQ ID NO: 51)
Primer 3: 5' CTCAAGTCCCTGCCCAGGCGCCTGCCTCACCCA 3'

(SEQ ID NO: 52)
Primer 4: 5'GGGGATATCCACCATGG(AG)ATG(CG)AGCTG(TG)
GT(CA)AT(CG)CTCTT 3'
```

After checking the point mutation at positions 40 and 42 by sequencing, mutations at positions 87 (83 according to Kabat's numbering) was introduced.

Primer for mutations at position 87 (83 according to Kabat's numbering) of the heavy chain:

```
                                          (SEQ ID NO: 53)
Primer 1: 5' CTCAGCAGGCTGCGGTCTGAGGACTCT 3'

(SEQ ID NO: 54)
Primer 2: 5' GGGGCTAGCTGAGGAGACTGTGAGAGTGGT 3'

(SEQ ID NO: 55)
Primer 3: 5' AGAGTCCTCAGACCGCAGCCTGCTGAG 3'

(SEQ ID NO: 56)
Primer 4: 5'GGGGATATCCACCATGG(AG)ATG(CG)AGCTG
          (TG)GT(CA)AT(CG)CTCTT 3'
```

Other replacements were not made because residues were involved in the three dimensional structure of the binding site.

The point mutations were verified by sequencing. The resulting construct was 1E10VHhu and it was cloned in PAH4604 expression vector. The resulting construct was 1E10 VH-PAH4604.

The analysis for VKIEI0 rendered also 3 amphipatic segments (FIG. 9); the first segment embraces FR1, the second one embraces CDR1 and the third one embraces FR3. It was decided to replace residues at positions 7, 8 and 15 by residues at the same position in the most homologous human sequence. The amino acids Thr, Thr and Leu were replaced by Ser, Pro and Val, respectively. The replacements were made by overlapping PCR (Kammann et al. (1989) Rapid insertional mutagenesis of DNA by polymerase chain reaction (PCR), Nucleic Acids Res., 17: 5404) using primers 1, 2, 3 and 4, whose sequences are the following:

Primers for mutations at positions 7, 8 and 15 of the light chain:

```
                                             (SEQ ID NO: 57)
Primer 1: 5'CAGATGACACAGTCTCCTTCCTCCCTGTCTGCCTCTGT
GGGAGA-CAGAGTC 3'

(SEQ ID NO: 58)
Primer 2: 5'AGCGTCGACTTACGTTT(TG)ATTTCCA(GA)CTT
(GT)GTCCC 3'

(SEQ ID NO: 59)
Primer 3: 5'GACTCTGTCTCCCACAGAGGCAGACAGGGAGGAAGGAG
ACTGTGTCATCTG 3'

(SEQ ID NO: 60)
Primer 4: 5'GGGGTTAACCACCATGAGG(GT)CCCC(-AT)GCTCA
G(CT)T(CT)CT(TG)GG(GA) 3'
```

The point mutations were verified by sequencing. The resulting construct was 1E10 Vkhu and it was cloned in PAG 4622 expression vector. The resultant construct was 1E10 VKhu-PAG4622.

To express the humanized antibody 1E10, NS-0 cells were transfected with 1E10 VHhu-PAH4604 and 1E10 VKhu-PAG4622.

1E10 humanized antibody was transfected following the same electroporation and detection procedure described previously for the chimeric antibodies.

Example 6

Biological Activity of Chimeric MAbIE10

The biological activity of the chimeric Mab 1E10 was tested by its specific binding to antigen as measured by ELISA.

For recombinant MAb 1 E10, Microtiter plates were coated with Mab P3. After washing with PBST (saline phosphate buffered solution containing 0.05% Tween 20), unspecific binding was blocked by incubating with 1% bovine sera albumin (BSA) in PBST for one hour at 37° C.

The wells were washed and incubated for 1 hour at 37° C. with purified recombinant Mab 1E10. The wells were washed with PBST and incubated with goat anti-human antibody conjugated with alkaline phosphatase at 37° C. for one hour. Finally, the wells were washed with PBST and substrate buffer containing p-nitrophenylphosphate was added. After half an hour, the absorbance was measured at 405 nm. Chimeric Mab C5 was used as negative control.

FIG. 10 shows the specific binding of chimeric Mab 1E10 to Mab P3.

BRIEF DESCRIPTION OF THE FIGURES

FIG. 1: VHP3 DNA and deduced amino acid sequences. Sequences are aligned according Kabat's numbering (Kabat et al. (1991), Sequences of proteins of immunological interest, Fifth Edition, National Institute of Health). CDRs are marked with dotted lines.

FIG. 2: VKP3 DNA and deduced amino acid sequences. Sequences are aligned according Kabat's numbering (Kabat and collaborators (1991), Sequences of proteins of immunological interest, Fifth Edition, National Institute of Health). CDRs are marked with dotted lines.

FIG. 3: VHP3 was aligned with the most homologous human sequence. Amphipatic segments are underlined and CDRs are in bold letters.

FIG. 4: VKP3 was aligned with the most homologous human sequence. Amphipatic segments are underlined and CDRs are in bold letters.

FIG. 5: Specific binding to GM3(NeuGc) by chimeric Mab P3. Different concentrations of Mab P3 and MAb TI (negative control) were tested by ELISA. Microtiter plates were coated with GM3(NeuGc) and GM3(NeuAc) (negative control) ganglioside in methanol and specific binding was measured.

FIG. 6: VH1E10 DNA and deduced amino acid sequences. Sequences are aligned according Kabat's numbering (Kabat and collaborators (1991), Sequences of proteins of immunological interest, Fifth Edition, National Institute of Health). CDRs are marked with dotted lines.

FIG. 7: VK1E10 DNA and deduced amino acid sequences. Sequences are aligned according Kabat's numbering (Kabat et al. (1991), Sequences of proteins of immunological interest, Fifth Edition, National Institute of Health). CDRs are marked with dotted lines.

FIG. 8: VH1E10 was aligned with the most homologous human sequence. Amphipatic segments are underlined and CDRs are in bold letters.

SEQUENCE LISTING

Figures 9, 10:
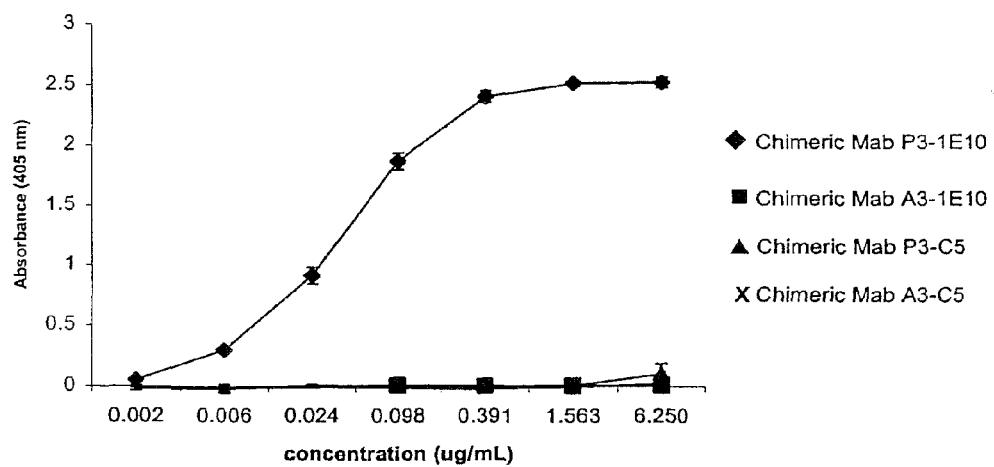
FIG. 9: VK1E10 was aligned with the most homologous human sequence. Amphipatic segments are underlined and CDRs are in bold letters.
FIG. 10: Specific binding of murine Mab P3 by chimeric Mab 1E10. Different concentrations of Mab 1E10 and MAb C5 (negative control) were tested by ELISA. Microtiter plates were coated with Mab P3 and Mab A3 (negative control) and specific binding was measured.

```
<160> NUMBER OF SEQ ID NOS: 72

<210> SEQ ID NO 1
<211> LENGTH: 5
<212> TYPE: PRT
<213> ORGANISM: Mus musculus
<220> FEATURE:
<221> NAME/KEY: DOMAIN
<222> LOCATION: (1)..(5)

<400> SEQUENCE: 1

Arg Tyr Ser Val His
1               5

<210> SEQ ID NO 2
<211> LENGTH: 16
```

```
<212> TYPE: PRT
<213> ORGANISM: Mus musculus
<220> FEATURE:
<221> NAME/KEY: DOMAIN
<222> LOCATION: (1)..(16)

<400> SEQUENCE: 2

Met Ile Trp Gly Gly Gly Ser Thr Asp Tyr Asn Ser Ala Leu Lys Ser
1               5                   10                  15

<210> SEQ ID NO 3
<211> LENGTH: 14
<212> TYPE: PRT
<213> ORGANISM: Mus musculus
<220> FEATURE:
<221> NAME/KEY: DOMAIN
<222> LOCATION: (1)..(14)

<400> SEQUENCE: 3

Ser Gly Val Arg Glu Gly Arg Ala Gln Ala Trp Phe Ala Tyr
1               5                   10

<210> SEQ ID NO 4
<211> LENGTH: 11
<212> TYPE: PRT
<213> ORGANISM: Mus musculus
<220> FEATURE:
<221> NAME/KEY: DOMAIN
<222> LOCATION: (1)..(11)

<400> SEQUENCE: 4

Lys Ala Ser Gln Asp Val Ser Thr Ala Val Ala
1               5                   10

<210> SEQ ID NO 5
<211> LENGTH: 7
<212> TYPE: PRT
<213> ORGANISM: Mus musculus
<220> FEATURE:
<221> NAME/KEY: DOMAIN
<222> LOCATION: (1)..(7)

<400> SEQUENCE: 5

Ser Ala Ser Tyr Arg Tyr Thr
1               5

<210> SEQ ID NO 6
<211> LENGTH: 9
<212> TYPE: PRT
<213> ORGANISM: Mus musculus
<220> FEATURE:
<221> NAME/KEY: DOMAIN
<222> LOCATION: (1)..(9)

<400> SEQUENCE: 6

Gln Gln His Tyr Ser Thr Pro Trp Thr
1               5

<210> SEQ ID NO 7
<211> LENGTH: 30
<212> TYPE: PRT
<213> ORGANISM: Mus musculus
<220> FEATURE:
<221> NAME/KEY: DOMAIN
<222> LOCATION: (1)..(30)

<400> SEQUENCE: 7

Gln Val Gln Leu Lys Glu Ser Gly Pro Gly Leu Val Ala Pro Ser Gln
```

```
              1               5                  10                 15
Ser Leu Ser Ile Thr Cys Thr Val Ser Gly Phe Ser Leu Ser
                    20                  25                 30

<210> SEQ ID NO 8
<211> LENGTH: 14
<212> TYPE: PRT
<213> ORGANISM: Mus musculus
<220> FEATURE:
<221> NAME/KEY: DOMAIN
<222> LOCATION: (1)..(14)

<400> SEQUENCE: 8

Trp Val Arg Gln Pro Pro Gly Lys Gly Leu Glu Trp Leu Gly
1               5                   10

<210> SEQ ID NO 9
<211> LENGTH: 32
<212> TYPE: PRT
<213> ORGANISM: Mus musculus
<220> FEATURE:
<221> NAME/KEY: DOMAIN
<222> LOCATION: (1)..(32)

<400> SEQUENCE: 9

Arg Leu Ser Ile Ser Lys Asp Asn Ser Lys Ser Gln Val Phe Leu Lys
1               5                   10                  15
Met Asn Ser Leu Gln Thr Asp Asp Thr Ala Met Tyr Tyr Cys Ala Arg
                    20                  25                  30

<210> SEQ ID NO 10
<211> LENGTH: 7
<212> TYPE: PRT
<213> ORGANISM: Mus musculus
<220> FEATURE:
<221> NAME/KEY: DOMAIN
<222> LOCATION: (1)..(7)

<400> SEQUENCE: 10

Trp Gly Gln Gly Thr Leu Val
1               5

<210> SEQ ID NO 11
<211> LENGTH: 23
<212> TYPE: PRT
<213> ORGANISM: Mus musculus
<220> FEATURE:
<221> NAME/KEY: DOMAIN
<222> LOCATION: (1)..(23)

<400> SEQUENCE: 11

Asp Ile Val Met Thr Gln Ser His Lys Phe Met Ser Thr Ser Val Gly
1               5                   10                  15
Asp Arg Val Ser Ile Thr Cys
                    20

<210> SEQ ID NO 12
<211> LENGTH: 15
<212> TYPE: PRT
<213> ORGANISM: Mus musculus
<220> FEATURE:
<221> NAME/KEY: DOMAIN
<222> LOCATION: (1)..(15)

<400> SEQUENCE: 12

Trp Tyr Gln Gln Lys Pro Gly Gln Ser Pro Lys Leu Leu Ile Tyr
1               5                   10                  15
```

```
<210> SEQ ID NO 13
<211> LENGTH: 32
<212> TYPE: PRT
<213> ORGANISM: Mus musculus
<220> FEATURE:
<221> NAME/KEY: DOMAIN
<222> LOCATION: (1)..(32)

<400> SEQUENCE: 13

Gly Val Pro Asp Arg Phe Thr Gly Ser Gly Ser Gly Thr Asp Phe Thr
1               5                   10                  15

Phe Thr Ile Ser Ser Val Gln Ala Glu Asp Leu Ala Val Tyr Tyr Cys
            20                  25                  30

<210> SEQ ID NO 14
<211> LENGTH: 7
<212> TYPE: PRT
<213> ORGANISM: Mus musculus
<220> FEATURE:
<221> NAME/KEY: DOMAIN
<222> LOCATION: (1)..(7)

<400> SEQUENCE: 14

Phe Gly Gly Gly Thr Lys Leu
1               5

<210> SEQ ID NO 15
<211> LENGTH: 5
<212> TYPE: PRT
<213> ORGANISM: Mus musculus
<220> FEATURE:
<221> NAME/KEY: DOMAIN
<222> LOCATION: (1)..(5)

<400> SEQUENCE: 15

Ser Tyr Asp Ile Asn
1               5

<210> SEQ ID NO 16
<211> LENGTH: 17
<212> TYPE: PRT
<213> ORGANISM: Mus musculus
<220> FEATURE:
<221> NAME/KEY: DOMAIN
<222> LOCATION: (1)..(17)

<400> SEQUENCE: 16

Trp Ile Phe Pro Gly Asp Gly Ser Thr Lys Tyr Asn Glu Lys Phe Lys
1               5                   10                  15

Gly

<210> SEQ ID NO 17
<211> LENGTH: 12
<212> TYPE: PRT
<213> ORGANISM: Mus musculus
<220> FEATURE:
<221> NAME/KEY: DOMAIN
<222> LOCATION: (1)..(12)

<400> SEQUENCE: 17

Glu Asp Tyr Tyr Asp Asn Ser Tyr Tyr Phe Asp Tyr
1               5                   10

<210> SEQ ID NO 18
```

```
<211> LENGTH: 11
<212> TYPE: PRT
<213> ORGANISM: Mus musculus
<220> FEATURE:
<221> NAME/KEY: DOMAIN
<222> LOCATION: (1)..(11)

<400> SEQUENCE: 18

Arg Ala Ser Gln Asp Ile Ser Asn Tyr Leu Asn
1               5                   10

<210> SEQ ID NO 19
<211> LENGTH: 8
<212> TYPE: PRT
<213> ORGANISM: Mus musculus
<220> FEATURE:
<221> NAME/KEY: DOMAIN
<222> LOCATION: (1)..(8)

<400> SEQUENCE: 19

Tyr Thr Ser Arg Leu His Ser Gly
1               5

<210> SEQ ID NO 20
<211> LENGTH: 9
<212> TYPE: PRT
<213> ORGANISM: Mus musculus
<220> FEATURE:
<221> NAME/KEY: DOMAIN
<222> LOCATION: (1)..(9)

<400> SEQUENCE: 20

Gln Gln Gly Asn Thr Leu Pro Trp Thr
1               5

<210> SEQ ID NO 21
<211> LENGTH: 30
<212> TYPE: PRT
<213> ORGANISM: Mus musculus
<220> FEATURE:
<221> NAME/KEY: DOMAIN
<222> LOCATION: (1)..(30)

<400> SEQUENCE: 21

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr
            20                  25                  30

<210> SEQ ID NO 22
<211> LENGTH: 14
<212> TYPE: PRT
<213> ORGANISM: Mus musculus
<220> FEATURE:
<221> NAME/KEY: DOMAIN
<222> LOCATION: (1)..(14)

<400> SEQUENCE: 22

Trp Val Arg Gln Arg Pro Glu Gln Gly Leu Glu Trp Ile Gly
1               5                   10

<210> SEQ ID NO 23
<211> LENGTH: 32
<212> TYPE: PRT
<213> ORGANISM: Mus musculus
<220> FEATURE:
<221> NAME/KEY: DOMAIN
<222> LOCATION: (1)..(32)
```

```
<400> SEQUENCE: 23

Lys Ala Thr Leu Thr Thr Asp Lys Ser Ser Thr Ala Tyr Met Gln
1               5                   10                  15

Leu Ser Arg Leu Thr Ser Glu Asp Ser Ala Val Tyr Phe Cys Ala Arg
                20                  25                  30

<210> SEQ ID NO 24
<211> LENGTH: 9
<212> TYPE: PRT
<213> ORGANISM: Mus musculus
<220> FEATURE:
<221> NAME/KEY: DOMAIN
<222> LOCATION: (1)..(9)

<400> SEQUENCE: 24

Trp Gly Gln Gly Thr Thr Leu Thr Val
1               5

<210> SEQ ID NO 25
<211> LENGTH: 23
<212> TYPE: PRT
<213> ORGANISM: Mus musculus
<220> FEATURE:
<221> NAME/KEY: DOMAIN
<222> LOCATION: (1)..(23)

<400> SEQUENCE: 25

Asp Ile Gln Met Thr Gln Thr Thr Ser Ser Leu Ser Ala Ser Leu Gly
1               5                   10                  15

Asp Arg Val Thr Ile Ser Cys
                20

<210> SEQ ID NO 26
<211> LENGTH: 15
<212> TYPE: PRT
<213> ORGANISM: Mus musculus
<220> FEATURE:
<221> NAME/KEY: DOMAIN
<222> LOCATION: (1)..(15)

<400> SEQUENCE: 26

Trp Tyr Gln Gln Lys Pro Asp Gly Thr Val Lys Leu Leu Ile Tyr
1               5                   10                  15

<210> SEQ ID NO 27
<211> LENGTH: 31
<212> TYPE: PRT
<213> ORGANISM: Mus musculus
<220> FEATURE:
<221> NAME/KEY: DOMAIN
<222> LOCATION: (1)..(31)

<400> SEQUENCE: 27

Val Pro Ser Arg Phe Ser Gly Ser Gly Ser Gly Thr Asp Tyr Ser Leu
1               5                   10                  15

Thr Ile Ser Asn Leu Glu Gln Glu Asp Ile Ala Thr Tyr Phe Cys
                20                  25                  30

<210> SEQ ID NO 28
<211> LENGTH: 10
<212> TYPE: PRT
<213> ORGANISM: Mus musculus
<220> FEATURE:
<221> NAME/KEY: DOMAIN
<222> LOCATION: (1)..(10)
```

<400> SEQUENCE: 28

Phe Gly Gly Gly Thr Lys Leu Glu Ser Lys
1               5                   10

<210> SEQ ID NO 29
<211> LENGTH: 39
<212> TYPE: DNA
<213> ORGANISM: Artificial Sequence
<220> FEATURE:
<223> OTHER INFORMATION: synthetic PCR primer sequence
<220> FEATURE:
<221> NAME/KEY: prim_transcript
<222> LOCATION: (1)..(39)
<223> OTHER INFORMATION: n=(c/t) and n=(a/g)
<220> FEATURE:
<221> NAME/KEY: misc_feature
<222> LOCATION: (11)..(11)
<223> OTHER INFORMATION: n is c or t
<220> FEATURE:
<221> NAME/KEY: misc_feature
<222> LOCATION: (25)..(26)
<223> OTHER INFORMATION: n is a or g

<400> SEQUENCE: 29
aggtctagaa nctccacaca caggnnccag tggatagac                                39

<210> SEQ ID NO 30
<211> LENGTH: 29
<212> TYPE: DNA
<213> ORGANISM: Artificial Sequence
<220> FEATURE:
<223> OTHER INFORMATION: synthetic PCR primer sequence
<220> FEATURE:
<221> NAME/KEY: prim_transcript
<222> LOCATION: (1)..(29)

<400> SEQUENCE: 30
gcgtctagaa ctggatggtg ggaagatgg                                           29

<210> SEQ ID NO 31
<211> LENGTH: 39
<212> TYPE: DNA
<213> ORGANISM: Artificial Sequence
<220> FEATURE:
<223> OTHER INFORMATION: synthetic PCR primer sequence
<220> FEATURE:
<221> NAME/KEY: prim_transcript
<222> LOCATION: (1)..(39)
<223> OTHER INFORMATION: n=(a/g) and n=(c/g) and n=(t/g) and n=(c/a) and
      n(c/g)
<220> FEATURE:
<221> NAME/KEY: misc_feature
<222> LOCATION: (18)..(18)
<223> OTHER INFORMATION: n is g or a
<220> FEATURE:
<221> NAME/KEY: misc_feature
<222> LOCATION: (22)..(22)
<223> OTHER INFORMATION: n is c or g
<220> FEATURE:
<221> NAME/KEY: misc_feature
<222> LOCATION: (28)..(28)
<223> OTHER INFORMATION: n is g or t
<220> FEATURE:
<221> NAME/KEY: misc_feature
<222> LOCATION: (31)..(31)
<223> OTHER INFORMATION: n is a or c
<220> FEATURE:
<221> NAME/KEY: misc_feature
<222> LOCATION: (34)..(34)
<223> OTHER INFORMATION: n is c or g

<400> SEQUENCE: 31 gggggatatcc accatggnat gnagctgngt natnctctt      39

<210> SEQ ID NO 32
<211> LENGTH: 30
<212> TYPE: DNA
<213> ORGANISM: Artificial Sequence
<220> FEATURE:
<223> OTHER INFORMATION: synthetic PCR primer sequence
<220> FEATURE:
<221> NAME/KEY: prim_transcript
<222> LOCATION: (1)..(30)

<400> SEQUENCE: 32
ggggctagct gcagagacag tgaccagagt      30

<210> SEQ ID NO 33
<211> LENGTH: 39
<212> TYPE: DNA
<213> ORGANISM: Artificial Sequence
<220> FEATURE:
<223> OTHER INFORMATION: synthetic PCR primer sequence
<220> FEATURE:
<221> NAME/KEY: prim_transcript
<222> LOCATION: (1)..(39)
<223> OTHER INFORMATION: n=(t/a) and n=(g/t) and n=(t/a) and n=(g/a)
<220> FEATURE:
<221> NAME/KEY: misc_feature
<222> LOCATION: (20)..(20)
<223> OTHER INFORMATION: n is t or a
<220> FEATURE:
<221> NAME/KEY: misc_feature
<222> LOCATION: (25)..(25)
<223> OTHER INFORMATION: n is g or t
<220> FEATURE:
<221> NAME/KEY: misc_feature
<222> LOCATION: (26)..(26)
<223> OTHER INFORMATION: n is a or t
<220> FEATURE:
<221> NAME/KEY: misc_feature
<222> LOCATION: (38)..(38)
<223> OTHER INFORMATION: n is g or a

<400> SEQUENCE: 33
ggggatatcc accatggagn cacannctca ggtctttnt      39

<210> SEQ ID NO 34
<211> LENGTH: 35
<212> TYPE: DNA
<213> ORGANISM: Artificial Sequence
<220> FEATURE:
<223> OTHER INFORMATION: synthetic PCR primer sequence
<220> FEATURE:
<221> NAME/KEY: prim_transcript
<222> LOCATION: (1)..(35)
<223> OTHER INFORMATION: n=(t/g) and n=(g/a) and n=(g/t)
<220> FEATURE:
<221> NAME/KEY: misc_feature
<222> LOCATION: (18)..(18)
<223> OTHER INFORMATION: n is g or t
<220> FEATURE:
<221> NAME/KEY: misc_feature
<222> LOCATION: (26)..(26)
<223> OTHER INFORMATION: n is g or a
<220> FEATURE:
<221> NAME/KEY: misc_feature
<222> LOCATION: (30)..(30)
<223> OTHER INFORMATION: n is g or t

<400> SEQUENCE: 34
agcgtcgact tacgtttnat ttccancttn gtccc      35

```
<210> SEQ ID NO 35
<211> LENGTH: 42
<212> TYPE: DNA
<213> ORGANISM: Artificial Sequence
<220> FEATURE:
<223> OTHER INFORMATION: synthetic PCR primer sequence
<220> FEATURE:
<221> NAME/KEY: prim_transcript
<222> LOCATION: (1)..(42)

<400> SEQUENCE: 35
atgacccagt ctccttcttc tctttccgcg tcagtaggag ac                             42

<210> SEQ ID NO 36
<211> LENGTH: 35
<212> TYPE: DNA
<213> ORGANISM: Artificial Sequence
<220> FEATURE:
<223> OTHER INFORMATION: synthetic PCR primer sequence
<220> FEATURE:
<221> NAME/KEY: prim_transcript
<222> LOCATION: (1)..(35)
<223> OTHER INFORMATION: n=(t/g) and n=(g/a) and n=(g/t)
<220> FEATURE:
<221> NAME/KEY: misc_feature
<222> LOCATION: (18)..(18)
<223> OTHER INFORMATION: n is g or t
<220> FEATURE:
<221> NAME/KEY: misc_feature
<222> LOCATION: (26)..(26)
<223> OTHER INFORMATION: n is g or a
<220> FEATURE:
<221> NAME/KEY: misc_feature
<222> LOCATION: (30)..(30)
<223> OTHER INFORMATION: n is g or t

<400> SEQUENCE: 36
agcgtcgact tacgtttnat ttccancttn gtccc                                     35

<210> SEQ ID NO 37
<211> LENGTH: 42
<212> TYPE: DNA
<213> ORGANISM: Artificial Sequence
<220> FEATURE:
<223> OTHER INFORMATION: synthetic PCR primer sequence
<220> FEATURE:
<221> NAME/KEY: prim_transcript
<222> LOCATION: (1)..(42)

<400> SEQUENCE: 37
gtctcctact gacgcggaaa gagaagaagg agactgggtc at                             42

<210> SEQ ID NO 38
<211> LENGTH: 39
<212> TYPE: DNA
<213> ORGANISM: Artificial Sequence
<220> FEATURE:
<223> OTHER INFORMATION: synthetic PCR primer sequence
<220> FEATURE:
<221> NAME/KEY: prim_transcript
<222> LOCATION: (1)..(39)
<223> OTHER INFORMATION: n=(t/a) and n=(g/t) and n=(t/a) and n=(g/a)
<220> FEATURE:
<221> NAME/KEY: misc_feature
<222> LOCATION: (20)..(20)
<223> OTHER INFORMATION: n is a or t
<220> FEATURE:
<221> NAME/KEY: misc_feature
<222> LOCATION: (25)..(25)
<223> OTHER INFORMATION: n is g or t
<220> FEATURE:
<221> NAME/KEY: misc_feature
<222> LOCATION: (26)..(26)
```

<223> OTHER INFORMATION: n is t or a
<220> FEATURE:
<221> NAME/KEY: misc_feature
<222> LOCATION: (38)..(38)
<223> OTHER INFORMATION: n is a or g

<400> SEQUENCE: 38
ggggatatcc accatggagn cacannctca ggtctttnt                              39

<210> SEQ ID NO 39
<211> LENGTH: 30
<212> TYPE: DNA
<213> ORGANISM: Artificial Sequence
<220> FEATURE:
<223> OTHER INFORMATION: synthetic PCR primer sequence
<220> FEATURE:
<221> NAME/KEY: prim_transcript
<222> LOCATION: (1)..(30)

<400> SEQUENCE: 39
ggggctagct gaggagactg tgagagtggt                                        30

<210> SEQ ID NO 40
<211> LENGTH: 30
<212> TYPE: DNA
<213> ORGANISM: Artificial Sequence
<220> FEATURE:
<223> OTHER INFORMATION: synthetic PCR primer sequence
<220> FEATURE:
<221> NAME/KEY: prim_transcript
<222> LOCATION: (1)..(30)

<400> SEQUENCE: 40
gcgtctagaa ctggatggtg ggaagatgga                                        30

<210> SEQ ID NO 41
<211> LENGTH: 39
<212> TYPE: DNA
<213> ORGANISM: Artificial Sequence
<220> FEATURE:
<223> OTHER INFORMATION: synthetic PCR primer sequence
<220> FEATURE:
<221> NAME/KEY: prim_transcript
<222> LOCATION: (1)..(39)
<223> OTHER INFORMATION: n=(a/g) and n=(c/g) and n=(t/g) and n=(c/a) and
      n=(c/g)
<220> FEATURE:
<221> NAME/KEY: misc_feature
<222> LOCATION: (18)..(18)
<223> OTHER INFORMATION: n is a or g
<220> FEATURE:
<221> NAME/KEY: misc_feature
<222> LOCATION: (22)..(22)
<223> OTHER INFORMATION: n is c or g
<220> FEATURE:
<221> NAME/KEY: misc_feature
<222> LOCATION: (28)..(28)
<223> OTHER INFORMATION: n is g or t
<220> FEATURE:
<221> NAME/KEY: misc_feature
<222> LOCATION: (31)..(31)
<223> OTHER INFORMATION: n is c or a
<220> FEATURE:
<221> NAME/KEY: misc_feature
<222> LOCATION: (34)..(34)
<223> OTHER INFORMATION: n is c or g

<400> SEQUENCE: 41
ggggatatcc accatggnat gnagctgngt natnctctt                              39

<210> SEQ ID NO 42

```
<211> LENGTH: 30
<212> TYPE: DNA
<213> ORGANISM: Artificial Sequence
<220> FEATURE:
<223> OTHER INFORMATION: synthetic PCR primer sequence
<220> FEATURE:
<221> NAME/KEY: prim_transcript
<222> LOCATION: (1)..(30)

<400> SEQUENCE: 42
ggggctagct gaggagactg tgagagtggt                               30

<210> SEQ ID NO 43
<211> LENGTH: 40
<212> TYPE: DNA
<213> ORGANISM: Artificial Sequence
<220> FEATURE:
<223> OTHER INFORMATION: synthetic PCR primer sequence
<220> FEATURE:
<221> NAME/KEY: prim_transcript
<222> LOCATION: (1)..(40)
<223> OTHER INFORMATION: n=(g/t) and n=(a/t) and n=(c/t) and n=(c/t) and
      n=(t/g) and n=(g/a)
<220> FEATURE:
<221> NAME/KEY: misc_feature
<222> LOCATION: (20)..(20)
<223> OTHER INFORMATION: n is g or t
<220> FEATURE:
<221> NAME/KEY: misc_feature
<222> LOCATION: (25)..(25)
<223> OTHER INFORMATION: n is a or t
<220> FEATURE:
<221> NAME/KEY: misc_feature
<222> LOCATION: (32)..(32)
<223> OTHER INFORMATION: n is c or t
<220> FEATURE:
<221> NAME/KEY: misc_feature
<222> LOCATION: (34)..(34)
<223> OTHER INFORMATION: n is c or t
<220> FEATURE:
<221> NAME/KEY: misc_feature
<222> LOCATION: (37)..(37)
<223> OTHER INFORMATION: n is g or t
<220> FEATURE:
<221> NAME/KEY: misc_feature
<222> LOCATION: (40)..(40)
<223> OTHER INFORMATION: n is g or a

<400> SEQUENCE: 43
ggggttaacc accatgaggn ccccngctca gntnctnggn                    40

<210> SEQ ID NO 44
<211> LENGTH: 35
<212> TYPE: DNA
<213> ORGANISM: Artificial Sequence
<220> FEATURE:
<223> OTHER INFORMATION: synthetic PCR primer sequence
<220> FEATURE:
<221> NAME/KEY: prim_transcript
<222> LOCATION: (1)..(35)
<223> OTHER INFORMATION: n=(t/g) and n=(g/a) and n=(g/t)
<220> FEATURE:
<221> NAME/KEY: misc_feature
<222> LOCATION: (18)..(18)
<223> OTHER INFORMATION: n is g or t
<220> FEATURE:
<221> NAME/KEY: misc_feature
<222> LOCATION: (26)..(26)
<223> OTHER INFORMATION: n is g or a
<220> FEATURE:
<221> NAME/KEY: misc_feature
<222> LOCATION: (30)..(30)
<223> OTHER INFORMATION: n is g or t

<400> SEQUENCE: 44
```
agcgtcgact tacgtttnat ttccancttn gtccc                          35

<210> SEQ ID NO 45
<211> LENGTH: 27
<212> TYPE: DNA
<213> ORGANISM: Artificial Sequence
<220> FEATURE:
<223> OTHER INFORMATION: synthetic PCR primer sequence
<220> FEATURE:
<221> NAME/KEY: prim_transcript
<222> LOCATION: (1)..(27)

<400> SEQUENCE: 45
caggttcagc tggtgcagtc tggagct                                   27

<210> SEQ ID NO 46
<211> LENGTH: 30
<212> TYPE: DNA
<213> ORGANISM: Artificial Sequence
<220> FEATURE:
<223> OTHER INFORMATION: synthetic PCR primer sequence
<220> FEATURE:
<221> NAME/KEY: prim_transcript
<222> LOCATION: (1)..(30)

<400> SEQUENCE: 46
ggggctagct gaggagactg tgagagtggt                                30

<210> SEQ ID NO 47
<211> LENGTH: 27
<212> TYPE: DNA
<213> ORGANISM: Artificial Sequence
<220> FEATURE:
<223> OTHER INFORMATION: synthetic PCR primer sequence
<220> FEATURE:
<221> NAME/KEY: prim_transcript
<222> LOCATION: (1)..(27)

<400> SEQUENCE: 47
agctccagac tgcaccagct gaacctg                                   27

<210> SEQ ID NO 48
<211> LENGTH: 39
<212> TYPE: DNA
<213> ORGANISM: Artificial Sequence
<220> FEATURE:
<223> OTHER INFORMATION: synthetic PCR primer sequence
<220> FEATURE:
<221> NAME/KEY: prim_transcript
<222> LOCATION: (1)..(39)
<223> OTHER INFORMATION: n=(a/g) and n=(c/g) and n=(t/g) and n=(c/a) and
      n=(c/g)
<220> FEATURE:
<221> NAME/KEY: misc_feature
<222> LOCATION: (18)..(18)
<223> OTHER INFORMATION: n is a or g
<220> FEATURE:
<221> NAME/KEY: misc_feature
<222> LOCATION: (22)..(22)
<223> OTHER INFORMATION: n is c or g
<220> FEATURE:
<221> NAME/KEY: misc_feature
<222> LOCATION: (28)..(28)
<223> OTHER INFORMATION: n is g or t
<220> FEATURE:
<221> NAME/KEY: misc_feature
<222> LOCATION: (31)..(31)
<223> OTHER INFORMATION: n is a or c
<220> FEATURE:
<221> NAME/KEY: misc_feature
<222> LOCATION: (34)..(34)

```
<223> OTHER INFORMATION: n is c or g

<400> SEQUENCE: 48 gggatatcc accatggnat gnagctgngt natnctctt                              39

<210> SEQ ID NO 49
<211> LENGTH: 33
<212> TYPE: DNA
<213> ORGANISM: Artificial Sequence
<220> FEATURE:
<223> OTHER INFORMATION: synthetic PCR primer sequence
<220> FEATURE:
<221> NAME/KEY: prim_transcript
<222> LOCATION: (1)..(33)

<400> SEQUENCE: 49
tgggtgaggc aggcgcctgg gcagggactt gag                                   33

<210> SEQ ID NO 50
<211> LENGTH: 30
<212> TYPE: DNA
<213> ORGANISM: Artificial Sequence
<220> FEATURE:
<223> OTHER INFORMATION: synthetic PCR primer sequence
<220> FEATURE:
<221> NAME/KEY: prim_transcript
<222> LOCATION: (1)..(30)

<400> SEQUENCE: 50
ggggctagct gaggagactg tgagagtggt                                       30

<210> SEQ ID NO 51
<211> LENGTH: 33
<212> TYPE: DNA
<213> ORGANISM: Artificial Sequence
<220> FEATURE:
<223> OTHER INFORMATION: synthetic PCR primer sequence
<220> FEATURE:
<221> NAME/KEY: prim_transcript
<222> LOCATION: (1)..(33)

<400> SEQUENCE: 51
ctcaagtccc tgcccaggcg cctgcctcac cca                                   33

<210> SEQ ID NO 52
<211> LENGTH: 39
<212> TYPE: DNA
<213> ORGANISM: Artificial Sequence
<220> FEATURE:
<223> OTHER INFORMATION: synthetic PCR primer sequence
<220> FEATURE:
<221> NAME/KEY: prim_transcript
<222> LOCATION: (1)..(39)
<223> OTHER INFORMATION: n=(a/g) and n=(c/g) and n=(t/g) and n=(c/a) and
      n=(c/g)
<220> FEATURE:
<221> NAME/KEY: misc_feature
<222> LOCATION: (18)..(18)
<223> OTHER INFORMATION: n is a or g
<220> FEATURE:
<221> NAME/KEY: misc_feature
<222> LOCATION: (22)..(22)
<223> OTHER INFORMATION: n is c or g
<220> FEATURE:
<221> NAME/KEY: misc_feature
<222> LOCATION: (28)..(28)
<223> OTHER INFORMATION: n is g or t
<220> FEATURE:
<221> NAME/KEY: misc_feature
<222> LOCATION: (31)..(31)
<223> OTHER INFORMATION: n is a or c
```

```
<220> FEATURE:
<221> NAME/KEY: misc_feature
<222> LOCATION: (34)..(34)
<223> OTHER INFORMATION: n is c or g

<400> SEQUENCE: 52
ggggatatcc accatggnat gnagctgngt natnctctt                                  39

<210> SEQ ID NO 53
<211> LENGTH: 27
<212> TYPE: DNA
<213> ORGANISM: Artificial Sequence
<220> FEATURE:
<223> OTHER INFORMATION: synthetic PCR primer sequence
<220> FEATURE:
<221> NAME/KEY: prim_transcript
<222> LOCATION: (1)..(27)

<400> SEQUENCE: 53
ctcagcaggc tgcggtctga ggactct                                               27

<210> SEQ ID NO 54
<211> LENGTH: 30
<212> TYPE: DNA
<213> ORGANISM: Artificial Sequence
<220> FEATURE:
<223> OTHER INFORMATION: synthetic PCR primer sequence
<220> FEATURE:
<221> NAME/KEY: prim_transcript
<222> LOCATION: (1)..(30)

<400> SEQUENCE: 54
ggggctagct gaggagactg tgagagtggt                                            30

<210> SEQ ID NO 55
<211> LENGTH: 27
<212> TYPE: DNA
<213> ORGANISM: Artificial Sequence
<220> FEATURE:
<223> OTHER INFORMATION: synthetic PCR primer sequence
<220> FEATURE:
<221> NAME/KEY: prim_transcript
<222> LOCATION: (1)..(27)

<400> SEQUENCE: 55
agagtcctca gaccgcagcc tgctgag                                               27

<210> SEQ ID NO 56
<211> LENGTH: 39
<212> TYPE: DNA
<213> ORGANISM: Artificial Sequence
<220> FEATURE:
<223> OTHER INFORMATION: synthetic PCR primer sequence
<220> FEATURE:
<221> NAME/KEY: prim_transcript
<222> LOCATION: (1)..(39)
<223> OTHER INFORMATION: n=(a/g) and n=(c/g) and n=(t/g) and n=(c/a) and
      n=(c/g)
<220> FEATURE:
<221> NAME/KEY: misc_feature
<222> LOCATION: (18)..(18)
<223> OTHER INFORMATION: n is a or g
<220> FEATURE:
<221> NAME/KEY: misc_feature
<222> LOCATION: (22)..(22)
<223> OTHER INFORMATION: n is c or g
<220> FEATURE:
<221> NAME/KEY: misc_feature
<222> LOCATION: (28)..(28)
<223> OTHER INFORMATION: n is g or t
<220> FEATURE:
```

```
<221> NAME/KEY: misc_feature
<222> LOCATION: (31)..(31)
<223> OTHER INFORMATION: n is a or c
<220> FEATURE:
<221> NAME/KEY: misc_feature
<222> LOCATION: (34)..(34)
<223> OTHER INFORMATION: n is c or g

<400> SEQUENCE: 56
ggggatatcc accatggnat gnagctgngt natnctctt                                  39

<210> SEQ ID NO 57
<211> LENGTH: 51
<212> TYPE: DNA
<213> ORGANISM: Artificial Sequence
<220> FEATURE:
<223> OTHER INFORMATION: synthetic PCR primer sequence
<220> FEATURE:
<221> NAME/KEY: prim_transcript
<222> LOCATION: (1)..(51)

<400> SEQUENCE: 57
cagatgacac agtctccttc ctccctgtct gcctctgtgg gagacagagt c                    51

<210> SEQ ID NO 58
<211> LENGTH: 35
<212> TYPE: DNA
<213> ORGANISM: Artificial Sequence
<220> FEATURE:
<223> OTHER INFORMATION: synthetic PCR primer sequence
<220> FEATURE:
<221> NAME/KEY: prim_transcript
<222> LOCATION: (1)..(35)
<223> OTHER INFORMATION: n=(t/g) and n=(g/a) and n=(g/t)
<220> FEATURE:
<221> NAME/KEY: misc_feature
<222> LOCATION: (18)..(18)
<223> OTHER INFORMATION: n is g or t
<220> FEATURE:
<221> NAME/KEY: misc_feature
<222> LOCATION: (26)..(26)
<223> OTHER INFORMATION: n is g or a
<220> FEATURE:
<221> NAME/KEY: misc_feature
<222> LOCATION: (30)..(30)
<223> OTHER INFORMATION: n is g or t

<400> SEQUENCE: 58
agcgtcgact tacgtttnat ttccancttn gtccc                                      35

<210> SEQ ID NO 59
<211> LENGTH: 51
<212> TYPE: DNA
<213> ORGANISM: Artificial Sequence
<220> FEATURE:
<223> OTHER INFORMATION: synthetic PCR primer sequence
<220> FEATURE:
<221> NAME/KEY: prim_transcript
<222> LOCATION: (1)..(51)

<400> SEQUENCE: 59
gactctgtct cccacagagg cagacaggga ggaaggagac tgtgtcatct g                    51

<210> SEQ ID NO 60
<211> LENGTH: 40
<212> TYPE: DNA
<213> ORGANISM: Artificial Sequence
<220> FEATURE:
<223> OTHER INFORMATION: synthetic PCR primer sequence
<220> FEATURE:
<221> NAME/KEY: prim_transcript
```

```
<222> LOCATION: (1)..(40)
<223> OTHER INFORMATION: n=(g/t) and n=(a/t) and n=(c/t) and
      n=(t/g) and n=(g/a)
<220> FEATURE:
<221> NAME/KEY: misc_feature
<222> LOCATION: (20)..(20)
<223> OTHER INFORMATION: n is g or t
<220> FEATURE:
<221> NAME/KEY: misc_feature
<222> LOCATION: (25)..(25)
<223> OTHER INFORMATION: n is a or t
<220> FEATURE:
<221> NAME/KEY: misc_feature
<222> LOCATION: (32)..(32)
<223> OTHER INFORMATION: n is c or t
<220> FEATURE:
<221> NAME/KEY: misc_feature
<222> LOCATION: (34)..(34)
<223> OTHER INFORMATION: n is c or t
<220> FEATURE:
<221> NAME/KEY: misc_feature
<222> LOCATION: (37)..(37)
<223> OTHER INFORMATION: n is g or t
<220> FEATURE:
<221> NAME/KEY: misc_feature
<222> LOCATION: (40)..(40)
<223> OTHER INFORMATION: n is g or a

<400> SEQUENCE: 60
ggggttaacc accatgaggn ccccngctca gntnctnggn                          40

<210> SEQ ID NO 61
<211> LENGTH: 118
<212> TYPE: PRT
<213> ORGANISM: Mus musculus
<220> FEATURE:
<221> NAME/KEY: DOMAIN
<222> LOCATION: (1)..(118)

<400> SEQUENCE: 61

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Arg Tyr
            20                  25                  30

Ser Val His Trp Val Arg Gln Pro Pro Gly Lys Gly Leu Glu Trp Leu
        35                  40                  45

Gly Met Ile Trp Gly Gly Gly Ser Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Ser Gly Val Arg Glu Gly Arg Ala Gln Ala Trp Phe Ala Tyr Trp
            100                 105                 110

Gly Gln Gly Thr Leu Val
        115

<210> SEQ ID NO 62
<211> LENGTH: 354
<212> TYPE: DNA
<213> ORGANISM: Mus musculus
<220> FEATURE:
<221> NAME/KEY: V_region
<222> LOCATION: (1)..(354)

<400> SEQUENCE: 62
caggtgcagc tgaaggagtc aggacctggc ctggtggcac cctcacagag cctgtccatc    60
```

```
acatgcactg tctctgggtt ctcattatcc agatatagtg tacactgggt tcgccagcct    120
ccaggaaagg gtctggagtg gctgggaatg atatggggtg gtggaagcac agactataat    180
tcagctctca aatccagact gagcatcagc aaggacaact ccaagagcca gttttctta     240 aaaatgaaca gtctgcaaac tgatgacaca gccatgtact actgtgccag aagtggggta    300
cgagagggaa gggcccaggc ctggtttgct tactggggcc aagggactct ggtc           354
```

```
<210> SEQ ID NO 63
<211> LENGTH: 104
<212> TYPE: PRT
<213> ORGANISM: Mus musculus
<220> FEATURE:
<221> NAME/KEY: DOMAIN
<222> LOCATION: (1)..(104)

<400> SEQUENCE: 63
```

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu
            100

```
<210> SEQ ID NO 64
<211> LENGTH: 312
<212> TYPE: DNA
<213> ORGANISM: Mus musculus
<220> FEATURE:
<221> NAME/KEY: V_region
<222> LOCATION: (1)..(312)

<400> SEQUENCE: 64
```

```
gacattgtga tgacccagtc tcacaaattc atgtccacat cagtaggaga cagggtcagc    60
atcacctgca aggccagtca ggatgtgagt actgctgtag cctggtatca acagaaacca    120
ggacaatctc ctaaactact gatttactcg gcatcctacc ggtacactgg agtccctgat    180
cgcttcactg gcagtggatc tgggacggat ttcacttca ccatcagcag tgtgcaggct     240
gaagacctgg cagtttatta ctgtcagcaa cattatagta ctccgtggac gttcggtgga    300
ggcaccaagc tg                                                        312
```

```
<210> SEQ ID NO 65
<211> LENGTH: 118
<212> TYPE: PRT
<213> ORGANISM: Mus musculus
<220> FEATURE:
<221> NAME/KEY: DOMAIN
<222> LOCATION: (1)..(118)

<400> SEQUENCE: 65
```

Gln Val Glu Leu Val Glu Ser Gly Gly Gly Val Val Glx Pro Gly Arg
1               5                   10                  15

Ser Leu Arg Leu Ser Cys Ala Ala Ser Gly Phe Thr Phe Ser Asn Tyr
            20                  25                  30

Ala Met His Trp Val Arg Gln Pro Gly Lys Gly Leu Glu Trp Val
        35                  40                  45

Ala Val Ile Ser Tyr Asx Gly Asx Asx Lys Tyr Tyr Ala Asx Ser Val
50                  55                  60

Lys Gly Arg Phe Thr Ile Ser Arg Asp Asx Ser Lys Asx Thr Leu Tyr
65                  70                  75                  80

Leu Gln Met Asn Ser Leu Arg Ala Glu Asx Thr Ala Val Tyr Tyr Cys
                85                  90                  95

Ala Arg Asp Arg Pro Leu Tyr Gly Asx Tyr Arg Ala Phe Asn Tyr Trp
            100                 105                 110

Gly Gln Gly Thr Leu Val
            115

<210> SEQ ID NO 66
<211> LENGTH: 103
<212> TYPE: PRT
<213> ORGANISM: Mus musculus
<220> FEATURE:
<221> NAME/KEY: DOMAIN
<222> LOCATION: (1)..(103)

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Thr Asn Tyr
            20                  25                  30

Asn Trp Phe Gln Gln Arg Pro Gly Gln Ala Pro Lys Val Leu Ile Tyr
        35                  40                  45

Gly Ala Ser Ile Leu Glu Thr Gly Val Thr Ser Arg Phe Ser Gly Ser
50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Tyr Asp Thr Leu Pro Leu Thr
                85                  90                  95

Phe Gly Gly Gly Thr Lys Val
            100

<210> SEQ ID NO 67
<211> LENGTH: 119
<212> TYPE: PRT
<213> ORGANISM: Mus musculus
<220> FEATURE:
<221> NAME/KEY: DOMAIN
<222> LOCATION: (1)..(119)

<400> SEQUENCE: 67

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Asp Ile Asn Trp Val Arg Gln Arg Pro Glu Gln Gly Leu Glu Trp Ile
        35                  40                  45

Gly Trp Ile Phe Pro Gly Asp Gly Ser Thr Lys Tyr Asn Glu Lys Phe
50                  55                  60

Lys Gly Lys Ala Thr Leu Thr Thr Asp Lys Ser Ser Ser Thr Ala Tyr
65                  70                  75                  80

```
Met Gln Leu Ser Arg Leu Thr Ser Glu Asp Ser Ala Val Tyr Phe Cys
                85                  90                  95

Ala Arg Glu Asp Tyr Tyr Asp Asn Ser Tyr Tyr Phe Asp Tyr Trp Gly
            100                 105                 110

Gln Gly Thr Thr Leu Thr Val
        115
```

<210> SEQ ID NO 68
<211> LENGTH: 357
<212> TYPE: DNA
<213> ORGANISM: Mus musculus
<220> FEATURE:
<221> NAME/KEY: V_segment
<222> LOCATION: (1)..(357)

<400> SEQUENCE: 68

```
caggttcagc tgcagcagtc tggagctgaa ctggtaaagc ctggggcttc agtgaagttg     60
tcctgcaagg cttctggcta caccttcaca agctatgata aaactgggt gaggcagagg    120
cctgaacagg gacttgagtg gattggatgg attttcctg agatggtag tactaagtac    180
aatgagaagt tcaagggcaa ggccacactg actacagaca atcctccag cacagcctac    240
atgcagctca gcaggctgac atctgaggac tctgctgtct atttctgtgc aagagaagac    300
tactatgata actcctacta ctttgactac tggggccaag gcaccactct cacagtc      357
```

<210> SEQ ID NO 69
<211> LENGTH: 107
<212> TYPE: PRT
<213> ORGANISM: Mus musculus
<220> FEATURE:
<221> NAME/KEY: DOMAIN
<222> LOCATION: (1)..(107)

<400> SEQUENCE: 69

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ser Lys
            100                 105
```

<210> SEQ ID NO 70
<211> LENGTH: 321
<212> TYPE: DNA
<213> ORGANISM: Mus musculus
<220> FEATURE:
<221> NAME/KEY: V_segment
<222> LOCATION: (1)..(321)

<400> SEQUENCE: 70

```
gatatccaga tgacacagac tacatcctcc ctgtctgcct ctctgggaga cagagtcacc     60
atcagttgca gggcaagtca ggacattagc aattatttaa actggtatca gcagaaacca   120
```

```
gatggaactg ttaaactcct gatctactac acatcaagat tacactcagg agtcccatca    180
aggttcagtg gcagtgggtc tggaacagat tattctctca ccattagcaa cctggagcaa    240
gaagatattg ccacttactt ttgccaacag gtaatacgc ttccgtggac gttcggtgga    300
ggcaccaagc tggaaatcaa a                                              321
```

<210> SEQ ID NO 71
<211> LENGTH: 126
<212> TYPE: PRT
<213> ORGANISM: Mus musculus
<220> FEATURE:
<221> NAME/KEY: DOMAIN
<222> LOCATION: (1)..(126)

<400> SEQUENCE: 71

Gln Thr Gln Leu Val Gln Ser Gly Ala Glu Val Arg Lys Pro Gly Ala
1               5                   10                  15

Ser Val Arg Val Ser Cys Lys Ala Ser Gly Ile Thr Phe Ile Asp Ser
                20                  25                  30

Tyr Ile His Trp Ile Arg Gln Ala Pro Gly His Gly Leu Glu Trp Val
            35                  40                  45

Gly Trp Ile Asn Pro Asn Ser Gly Gly Pro Asn Tyr Ala Pro Arg Phe
        50                  55                  60

Gln Gly Arg Val Thr Met Thr Arg Asp Ala Ser Phe Ser Thr Ala Tyr
65                  70                  75                  80

Met Asp Leu Arg Ser Leu Arg Ser Asp Asp Ser Ala Val Phe Tyr Cys
                85                  90                  95

Ala Lys Ser Asp Pro Phe Trp Ser Asp Tyr Tyr Asn Phe Asp Tyr Ser
            100                 105                 110

Tyr Thr Leu Asp Val Trp Gly Gln Gly Thr Thr Val Thr Val
        115                 120                 125

<210> SEQ ID NO 72
<211> LENGTH: 107
<212> TYPE: PRT
<213> ORGANISM: Mus musculus
<220> FEATURE:
<221> NAME/KEY: DOMAIN
<222> LOCATION: (1)..(107)

<400> SEQUENCE: 72

Asp Ile Gln Met Thr Glx Ser Pro Ser Ser Leu Ser Ala Ser Val Gly
1               5                   10                  15

Asx Arg Val Thr Ile Thr Cys Arg Ala Ser Glx Thr Ile Ser Ser Tyr
                20                  25                  30

Leu Asx Trp Tyr Glx Glx Lys Pro Gly Lys Ala Pro Asx Leu Leu Ile
            35                  40                  45

Tyr Ala Ala Ser Asx Leu His Ser Gly Val Pro Ser Arg Phe Ser Gly
        50                  55                  60

Ser Gly Ser Gly Thr Asx Phe Thr Phe Thr Ile Ser Ser Leu Glx Pro
65                  70                  75                  80

Glx Asx Phe Ala Thr Tyr Tyr Cys Glx Glx Ser Tyr Ser Ser Pro Thr
                85                  90                  95

Thr Phe Gly Glx Gly Thr Arg Leu Glx Ile Lys
            100                 105

What is claimed is:

1. A humanized monoclonal antibody derived from murine anti-idiotypic monoclonal antibody 1E10, said murine anti-idiotypic monoclonal antibody 1E10 being produced by an hybridoma cell line with deposit number ECACC 97112901 and recognizing monoclonal antibody P3 ("Mab P3"), said Mab P3 being produced by hybridoma cell line with deposit number ECACC 94113026, wherein said humanized monoclonal antibody derived from murine anti-idiotypic monoclonal antibody 1E10 comprises:
   (a) a heavy chain constant region of human gamma-1 chain;
   (b) a light chain constant region of human kappa chain;
   (c) heavy chain variable region hypervariable domains (CDRs) comprising the following sequences:
CDR1: SYDIN (SEQ ID NO: 15);
CDR2: WIFPGDGSTKYNEKFKG (SEQ ID NO: 16);
CDR3: EDYYDNSYYFDY (SEQ ID NO: 17);
   (d) light chain variable region CDRs comprising the following sequences:
CDR1: RASQDISNYLN (SEQ ID NO: 18);
CDR2: YTSRLHSG (SEQ ID NO: 19);
CDR3: QQGNTLPWT (SEQ ID NO: 20);
   (e) heavy chain variable region framework regions (FRs) comprising the following sequences: FR1: QVQLQQS-GAELVKPGASVKLSCKASGYTFT (SEQ ID NO: 21);
FR2: WVRQRPEQGLEWIG (SEQ ID NO: 22);
FR3: KATLTTDKSSSTAYMQLSRLTSEDSAVYFCAR (SEQ ID NO: 23);
FR4: WGQGTTLTV (SEQ ID NO: 24);
   (f) light chain variable region FRs comprising the following sequences:
FR1: DIQMTQTTSSLSASLGDRVTISC (SEQ ID NO: 25);
FR2: WYQQKPDGTVKLLIY (SEQ ID NO: 26);
FR3: VPSRFSGSGSGTDYSLTISNLEQEDIATYFC (SEQ ID NO: 27);
FR4: FGGGTKLESK (SEQ ID NO: 28); and
   (g) further comprising at least one of the following substitutions in the FRs: LIGHT CHAIN variable region FRs:
Position 7 in SEQ ID NO: 25: Thr by Ser;
Position 8 in SEQ ID NO: 25: Thr by Pro;
Position 15 in SEQ ID NO: 25: Leu by Val;
HEAVY CHAIN variable region FRs:
Position 5 in SEQ ID NO: 21: Gln by Val;
Position 5 in SEQ ID NO: 22: Arg by Ala;
Position 7 in SEQ ID NO: 22: Glu by Gly;
Position 21 in SEQ ID NO: 23: Thr by Arg.

2. An isolated cell line that produces the humanized monoclonal antibody of claim 1.

3. A pharmaceutical composition for treating malignant breast tumors and melanomas, their metastases and relapses, said composition comprising the humanized monoclonal antibody of claim 1.

* * * * *